(12) United States Patent
Cohen

(10) Patent No.: US 10,300,226 B2
(45) Date of Patent: May 28, 2019

(54) RESCUE INHALER

(71) Applicant: Binyomin Cohen, Brooklyn, NY (US)

(72) Inventor: Binyomin Cohen, Brooklyn, NY (US)

( * ) Notice: Subject to any disclaimer, the term of this patent is extended or adjusted under 35 U.S.C. 154(b) by 1013 days.

(21) Appl. No.: 14/739,476

(22) Filed: Jun. 15, 2015

(65) Prior Publication Data
US 2016/0361508 A1 Dec. 15, 2016

(51) Int. Cl.
| A61M 11/04 | (2006.01) |
| A61M 15/00 | (2006.01) |
| A61M 16/10 | (2006.01) |
| A61M 16/12 | (2006.01) |
| A61M 16/14 | (2006.01) |
| A61M 16/18 | (2006.01) |

(52) U.S. Cl.
CPC ...... *A61M 15/0003* (2014.02); *A61M 11/042* (2014.02); *A61M 15/002* (2014.02); *A61M 15/0021* (2014.02); *A61M 16/109* (2014.02); *A61M 16/12* (2013.01); *A61M 16/147* (2014.02); *A61M 16/18* (2013.01); *A61M 15/0018* (2014.02); *A61M 2202/025* (2013.01); *A61M 2202/0208* (2013.01); *A61M 2202/0266* (2013.01); *A61M 2202/048* (2013.01); *A61M 2205/3653* (2013.01); *A61M 2205/8206* (2013.01); *A61M 2205/8225* (2013.01)

(58) Field of Classification Search
CPC ............ A61M 15/0003; A61M 11/042; A61M 15/002; A61M 15/0021; A61M 16/109; A61M 16/147; A61M 16/12; A61M 16/18; A61M 15/0018; A61M 2202/0208; A61M 2202/025; A61M 2202/0266; A61M 2202/048; A61M 2205/8206; A61M 2205/8225
See application file for complete search history.

(56) References Cited

U.S. PATENT DOCUMENTS

| 4,008,716 A * | 2/1977 | Amlong | A62B 9/02 128/205.24 |
| 5,755,220 A * | 5/1998 | Ando | A61M 16/104 128/203.12 |
| 6,834,778 B2 * | 12/2004 | Jinbo | B65D 83/68 132/112 |
| 7,021,499 B2 * | 4/2006 | Hansen | A47L 13/00 222/135 |

(Continued)

*Primary Examiner* — Gregory A Anderson
*Assistant Examiner* — Jonathan S Paciorek

(57) ABSTRACT

A portable rescue inhaler having a first canister containing a gas mixture of helium, oxygen, and nitrogen, and having a second canister containing an aerosolized medicine. The gas mixture of helium, oxygen, and nitrogen contained in the first canister has a density slightly lower than the density of atmospheric air. The portable rescue inhaler is capable of delivering the lower density gas mixture simultaneously with the aerosolized medicine for emergency hand held rescue of patients suffering from asthma, asthmatic bronchitis, COPD, emphysema, cystic fibrosis, and myocardial insufficiency. The portable rescue inhaler is capable of providing a vaporized anesthetic for greater medical assistance for patients in need of anesthesia due to respiratory insufficiency. The portable rescue inhaler reduces intraoperative risks in respiratory patients prior to gaining access to a hospital or care center.

20 Claims, 7 Drawing Sheets

(56) References Cited

U.S. PATENT DOCUMENTS

2006/0213514 A1* 9/2006 Price ................. A61M 15/0028
                                                128/203.15
2008/0087280 A1* 4/2008 Dhuper ............... A61M 15/009
                                                128/200.23

* cited by examiner

RESCUE INHALER

The present application claims the benefit under 35 U.S.C. 119(e) of U.S. Provisional application Ser. No. 14/120,655, filed on Jun. 13, 2014 and incorporates the same by reference.

BACKGROUND OF THE INVENTION

The rational for the present invention is based upon several factors that interplay against the transmittal of oxygen and removal of carbon dioxide.

Many patients with COPD adopt a rapid, shallow breathing pattern, frequently with chest wall and abdominal asynchrony. In patients with hyper-inflated lungs and an increased expiratory reserve volume (ERV), the inspiratory muscles are in a permanently shortened position which creates a poor length-tension relationship.

Despite some adaptation of the muscles to this shortening, inhalation is augmented by the accessory muscles of respiration, with fixation of the shoulder girdle. Although by fixing the shoulder girdle, thoracic volume can be increased and ventilation improved, respiratory muscle oxygen consumption is increased.

By using an anesthetic along with gases having a reduced density supplemented with increased oxygen, rates of flow of gas time travel are reduced and the resistance encountered by COPD patients is relieved by the reduced density of gases within the conducting airways. Using too much reduced density adversely affects the flow and the pressure in the deepest lung fields which are left shut, and bypassed.

Historically, using very low density heliox in COPD patients allows ease of work of breathing, but decreasing the density of the gases too low, increases the velocity in blocked and semi-blocked communicating airways having reduced diameters causing increased turbulence resulting in forward eddy formation and causing air clutching and nondelivery of critically fresh inhaled gases. This braking of the air just behind the forward fast gases causes back pressure and increases pressure to slow the transmittal of gases. This increases inspiratory time, thus further limiting exhalation time and the removal of waste gases. Slowing the transmittal of gases prevents the opening up of collapsed and unexpanded alveoli in the depth of the lung fields.

High heliox concentrations, meaning concentrations having helium above 60 percent, increase turbulence by reducing the gas density such that its velocity in damaged, blocked, and semi-blocked distal airways found in the lower airways of the lungs in combination due to the increased lung volumes found above normal, there in the most distal communicating airways closest to the alveoli, where actual gas exchange between outside air and internal bloodstream occurs, the pressure driving gases is factually increased as is the resistance to local airflow. It is here that the radius and density becomes highly relevant to COPD patients. Therefore, the present invention reduces the density of heliox, but reduces the density moderately such that it is near the density of air which allows for the greatest push per volume change in the areas most proximal to the gas exchange pores, known as "pores of khan", contained within the alveoli where actual gas exchange of air inhaled from outside the lungs enters the bloodstream and supplies needed oxygen to counter the muscular increases of oxygen usages found.

Many patients who have complications related to obstructive and/or restrictive airways experience increased damage to the lung's elastic ability. Obstructive airway diseases involve the two large bronchi, left and right branches and down, via multiple generations of branching smaller communicating airways. Such airway generation branching is commonly considered to have 23 generations that reach into the lung fields down until the "Alveoli"—the lungs 'air sac's,' where blood-air-gas-exchange occurs.

Chronic obstructive pulmonary (airway) disease, known as C.O.P.D., includes dysfunctions of those airways also termed "airway disease" which includes asthma, emphysema, secondary pulmonary restrictions, and obstructive components to airflow as found in lung parenchyma fibrosis and cystic fibrosis.

As well as following lung disease, segmental resections and or post chest wall traumas, fall under this encompassing title, specifically in this application most under common medical heading's of Chronic Obstructive Pulmonary Disease ("COPD").

Two types of inhaling medical devices are currently used for treating patients experiencing breathing difficulties. One device, typically given at a hospital, is known as a hand held nebulizer or HHN. This type of device uses a large metal tank connected to an oxygen line for supplying oxygen to the patient. This type of device is not portable.

The other device is a portable device used out of hospital commonly called a "rescue inhaler" and also known as a metered-dose inhaler or MDI. Both devices dispense inhaled drugs in the form of an aerosolized medication, typically airway opener drugs which are designed to open lung airways which carry air to the recesses of the lungs where the fresh air interacts with the air sacs within the lung tissue. These airway opener drugs are given to counteract airway spasms and or constrictions.

Both types of inhalers usually spray into the user's mouth. Said aerosolized medication is designed to combat airway spasms and diameter changes within the lung's airways when inhaled. Without such treatments, a patient will have to increase their work of breathing and rate of breaths in order to supply oxygen to their lungs. At severe times, patients are unable to breathe on their own without the assistance of such devices, and if left untreated, will go into respiratory failure requiring them to be placed onto a ventilator for supportive breathing along with oxygenation supplementation.

Thus, airway opening drugs are dispensed as an aerosol under pressure and are inhaled by a patient to aid breathing which has been affected by airway flow restrictions due to asthma, bronchitis, emphysema, asthmatic bronchitis, cystic fibrosis, and chronic or acute allergic complications.

Metered-dosage inhalers carry medicine within a light metal pressurized canister. Such medicine is usually an aerosolized medicine typically consisting of a beta-adrenergic designed airway opening drug. Some examples include Salbutamol and Albuterol. These aerosolized medications are sprayed outward toward a user's mouth for inhalation Inhaled aerosolized steroids may also be used.

Without such devices along with their inhaled drugs, patients would suffocate thus leading them to be hospitalized, intubated, and placed onto ventilatory support. An exacerbation of asthma, when severe, is life threatening.

Typically mediations inhaled by prior art units such as an MDI are dispensed in a pre-selected quantity that is not always optimum for a patient's airways. This is due to medication being lost from impacting the back of the throat during the higher inspiratory phase of the respiratory cycle. This could lead to a greater cardio tropic effect which is dangerous: the lost medicine contacting the throat of the patient produces a greater load on the heart due to the large amount of blood vessels at back of the throat. The danger occurs physiologically when such medicines dissolve into the blood vessels in the back of the throat when lost as during the higher inspiratory phase. In this case, a hand held nebulizer is better than a metered-dose inhaler because it delivers a lower quantity of medication over time which allows the airways to progressively open at lower dosages.

However, hand held nebulizer cannot be carried by an individual person, such as for when they are walking down the street, because they are much less portable than a metered-dose inhaler. Rather, a patient is most commonly transported on emergency basis to a hospital where they receive a hand held nebulizer treatment. Hand held nebulizers provide longer treatment times by continuously spraying aerosolized medicine for inhalation by the patient. This allows for better treatment for reversing and stabilizing airway deficiencies above that of a metered-dose inhaler where each spray is activated by the user as a push on the medicine canister into its canister holder.

Hand held nebulizers are the standard treatment modality when an individual is hospitalized. Typically, respiratory therapy departments will instruct staff to give hand held nebulizer treatments to their hospitalized patients according to a time schedule. Such time schedules are often inappropriate to the condition of the patient at the time the staff arrives to implement the treatment because the patient may not require a treatment at that time. Yet, the patient may still receive the hand held nebulizer treatment as a prophylactic measure which, although is logically sound, is inherently harmful because it may lead to overwork of the patient's cardiac system and the patient's airways often become less responsive to the drugs dispensed by the hand held nebulizer.

In view of the above, patients are the best to judge their air way hunger and insufficiency at a particular time, and are in the best position to know when to give themselves an HHN treatment. However, patients, such as those in a hospital setting, are often unable to give themselves HHN treatment because they are restricted by IV lines and other medical instruments, and are also often immobile due to a physical condition.

As a consequence, patients suffer by having to take an HHN treatment when many times they are asymptomatic and not in need. This is also unfavorable for caregivers who have to care for other patients, but are required by hospital metrics and third-party reimbursement rates to give the HHN treatments to patients who are clearly asymptomatic and do not need HHN treatment. Thus, irregardless of the patient's actual airway status, HHN treatments are given even though the patient may experience increase heart rates, nervousness, and lack of sleep. This may also lead patient to develop tachyphylaxis which is a decreased response to the medicine given over a period of time so that larger doses are required to produce the same response.

The powering of a hand held nebulizer is typically by compressed air or oxygen supplied by transfer lines running through a hospital's walls, and having an outlet next to a patient's bedside. Said gases are compressed prior to release and are supplied from outside the hospital, either by a band of high pressure gas cylinders connected to a common outlet controller or supplied by a bulk system such as a liquid gas oxygen supply, which in tandem with a vaporizer, supply the oxygen gas to the hospital.

The hand held nebulizer is connected to the patient's bedside with a transport tube providing air or oxygen from an oxygen or air outlet attached via a flow meter designated for each gas. The transport tube is a thin walled supply hose that connects to the gas outlet for supplying the compressed air or oxygen to the patient, and thus powers the hand held nebulizer pneumatically.

There are electrical powered hand held nebulizers, but these nebulizers are still connected to a compressed air almost exclusively without oxygen supply for supplying the gas mixture to the patient. The hand held nebulizer has a reservoir cup where the liquid medicine is placed at a specific dose which is determined and supplied by a self-contained plastic dosage container with a removable top used to fill the nebulizer reservoir. Once the reservoir is filled, the medicine dosage container is discarded. The medicine is then suctioned up via capillary action and brought to a jet nozzle designed for atomization of the contained medicine so that it can be sprayed in small particles as an aerosol.

From these combined parts and actions (e.g., capillary suction and a jet nozzle powered by an external gas supply), an aerosol is generated for the patient to inhale by holding the nebulizer to his/her mouth if capable. Otherwise, a health care provider may assist the patient in holding the nebulizer. In another form, a user wears a mask for inhaling the aerosol medication from the nebulizer. In either form, a patient inhales the aerosol with the suspended medicine at the patient's rate of breathing, called respiratory rate, and depth, called tidal volume.

In contrast to the nebulizer, a metered dosage inhaler has within itself the powering mechanism which is a self-contained cartridge under pressure having a propellant along with the medicine to be inhaled.

SUMMARY OF THE INVENTION

An object of the present invention is to incorporate the benefits of metered-dosage inhalers with the option to provide supplemental oxygen while simultaneously decreasing the density for delivering the airway opening drug and/or medicines. As a direct result of the reduction in density, the airway opening drug and/or medicines can reach and penetrate into the most affected distal airways to achieve the optimal benefit of such airway opening drug and/or medicine such as antibiotic drug(s) used. Another object is to have the ability to provide anesthetic gases with those of both longer acting hand held nebulizers and rescue inhalers for dispensing less airway opener drug in a smaller quantity in a given time.

In order to achieve the above benefits, it is contemplated the usage of a compressed combination of pre-selected gases, held under pressure within a container, in a device that also has the option to use either in conjunction with or alone anesthetic gases. The claimed rescue inhaler device can achieve greater relief of bronchospasm and other contributory conditions that would cause bronchospasm to be unremitting under typical MDI and HHN therapy. Thus, the claimed rescue inhaler device, which is fully portable, can relieve the work of breathing for diseased individuals having respiratory complications.

It is further contemplated a device that incorporates the usage of multiple compartments having a common connection such that each may contribute to the other by allowing the flow of pre-selected gas combinations to enhance the passage of an aerosol. Thus, said device has the ability to lower the density of a carrier gas in conjunction with a generated aerosol such that deposition and penetration of said aerosol is made greater even for those with weakened inhalation ability and strengths.

A device that functions as a portable anesthesia unit that may be utilized out of hospital and in the field such as in an army's need during battle is contemplated.

It is further contemplated a device with means to use a cheaper method for dispensing an anesthesia contained in liquid form within pre-selected packets, herein called "anesthesia envelopes." Said envelopes dissolve in short time when heat is applied to said envelope for releasing its contents. A pre-measured quantity of anesthetic is diluted to a concentration and volume for giving a specific amount of anesthesia. Said anesthesia, contained as a liquid, is transformed by the applied heat into an anesthetic gas prior to being inhaled through said device.

Another embodiment of the present invention includes a method for storing and providing a cheaper, more cost effective usage of anesthesia drugs protected from environmental temperature changes, by having said anesthesia drugs insulted by a wax or sugar envelope acting as insulator and container.

It is also envisioned a method and technique using a device for easing the work and speed of breathing by COPD patients by removing retained CO2 gases in the COPD patients and by making a more normalized blood pH. While oxygen alone reduces breathlessness, heliox reduces resistance in the lungs during exhalation which allows COPD patients to exhale more air. This can allow the air sacs within the patient's lungs to more effectively eliminate greater amounts of retained carbon dioxide.

An objective of the present invention is to reduce the number of hospital admissions for individuals suffering from COPD, asthma, and bronchitis. This objective is obtained by the alleviation in such patient populations of breathing difficulties when these patient populations experience either critical or exacerbating breathing conditions.

It is further envisioned a device that has the ability to provide greater volume for each inhalation by individuals in a weakened state who cannot generate a good negative inspiratory tug at inhalation due to reduced airway diameters. Said device uses bronchodilator agents such as aerosol combined with a low density gas thereby allowing the patient to expend less work effort for breathing while simultaneously getting more volume for each negative inspiratory pull.

An additional object of the present invention is to make use of gas cartridges having mixed anesthetic gases under a helium environment to diminish the gases density, as anesthetic gases have much higher densities than air and oxygen. This provides the benefit of improving inhalation through the device.

Due to the known reduction in functional residual capacity, "FRC", which is especially critical in COPD patients, in conjunction with the inhaled anesthetics is an application of a heliox mixture via the common airflow conduit. This reduces the over enlarged functional residual capacity thus adding beneficial effects by decreasing airway resistance and improving the exhaled volume of such patient population reducing the retained $CO_2$ built up over time in the lungs of COPD patents.

A further benefit of the present invention is improved cardio protective effects by supplying readily available portable oxygen and providing the option to inhale anesthetic gases for breaking refractory spasms without over-usage of air opener drugs effecting cardiac stability. Such benefits are not present in any currently known nebulizers or metered-dosage inhalers.

A further object of the present invention is to achieve conscious sedation via pre-selected anesthesia gases, either in nontoxic inhalable wax or sugar envelope or contained within a miniature cylinder under pressure. The present invention is designed to reduce by a safe range from 18 to 30% of MAC, allowing for a full three to eight minutes exposure time to produce a state of relaxation and/or pain relief. This can achieve a greater and deeper breath, not only breaking airway spasms, but also allowing for greater aerosol penetration and myocardial protection in the patient while also simultaneously achieving a greater depth and coverage throughout the respiratory tracheobronchial tree by using anesthetic gases along with either bronchodilator therapy and/or heliox as an aerosol gas carrier.

A further object of the present invention is to provide a greater control and measure of anesthetic gases to be vaporized and provided to a patient during induction and/or during the procedure requiring such sedation or anesthetic gases.

Another objective of the present invention is to reduce the toxicity and costs of utilizing Heliox therapy by usage of pre-selected concentrations of heliox as carrier gas in pressurized pre-selected cylinders or envelopes of wax or sugar readily exchanged.

A further object of the invention is to provide several different kinds of anesthetic gases within a single carrier vehicle thereby providing for greater control and usage of anesthetic gases while saving space, and cost and achieving greater efficiency.

A further object of the present invention is to provide greater periods of time to save patients in respiratory difficulty than existed before.

The invention allows the use of heliox to be more effective by increasing the target gas density. In the past, heliox generally comprised 80% helium and 20% oxygen, or 70% helium and 30% oxygen. This resulted in the negative consequence, as explained above, of limiting air flow to the most distal communicating airways where flow via laminar state is absolutely critical to the region of the lung fields of a patient. Thus, an object of the invention is to use specifically designed gas mixtures using lower levels of helium combined with specific limited levels of oxygen and nitrogen to achieve a slightly lower density of inhaled gas than that of atmospheric air and/or supplemental pure oxygen. Another object of the present invention is to use these designed gas mixtures along with anesthetic gas(es) within a suitable envelope, wax, sugar, or wafer with known resistance to current flow. When being utilized at reduced values of the known MAC for the agent used, such reductions diminish, but do not eliminate, the gag and swallow reflexes of users of the present invention.

An additional object of the present invention is the usage of such reduced percentages of Heliox and reduced Nitrogen to achieve the greater benefits of a balance between the density and viscosity of heliox for the patient's benefit. Thus, an application of the present invention limits heliox concentrations to achieve the optimal benefits struck as a balance between the diminished gas density of Helium and the greater viscosity of Helium for COPD patients experiencing restrictive breathing flow conditions. This maximizes greater dynamic kinematic physiological breathing benefits for mid-expiratory and end-expiratory flow from weakened and spastic airways as seen in COPD patients. The present invention is thus designed to allow for greater ventilation perfusion ratios which have not yet achieved by the prior art.

Another object of the invention is to utilize a venire control linked via knob to a lower supply reservoir of helium to mix with the oxygen percentage line thus choosing and lowering the density of the gas density via a ventilator.

Another objective of the present invention is the use of limited heliox with anesthetic gases inhaled both for the spontaneous breathing and for the totally-supported-on-ventilator patient populations for allowing a larger and healthier FRC then prior uses of higher levels of heliox typically achieved. In patients who are spontaneously breathing, inhaled anesthetics can reduce both tidal volume and minute ventilation and cause tachypnea, resulting in increased work of breathing. However, titrating the quantity with a bronchodilating agent and low density gas while limiting the opposite effects of the gases viscosity obviates such responses even in a sensitive patient.

By using lower heliox concentrations, the present invention can achieve the benefit of increasing the depth of breathing and the reduction of CO2 retention simultaneously in the obstructive type COPD patient populations. This results in a greater decrease in the respiratory rate of patients with COPD.

A further object of the present invention is to use anesthetic gases and or heliox in limited concentrations always lower than 65% concentration for powering and/or assisting as a carrier gas in both MDI and HHN units hereto unused and untaught in the art. Awareness of laminar flow in the peripheral airways is often neglected as to the driving pressure and the distension of the hyper inflated lungs.

Another objective of the present invention is to have two mechanisms for providing the ability to affect a direct functional relationship between airway diameter and resistance to flow/time. A benefit of the present invention is that it can alter viscosity as well velocity to the airways.

Typically, ambient air is comprised of gases having the following concentrations: nitrogen 79.5%, oxygen 20.93%, carbon dioxide 0.034%, xenon 0.005%, krypton 0.0002%, and helium 0.003%. Air density is affected by the air pressure, temperature and humidity. The density of the air is reduced by decreased air pressure, increased temperatures and increased moisture. The present invention uses artificially designed mixtures, such as a two gas mixture of helium and oxygen, or three and four gas mixtures with specific ratios to achieve a calculated compressed gas density as the propellant to simultaneously achieve greater airway communication penetrations of medicine while increasing ventilation to perfusion matching ("V/Q matching"), so commonly and clinically found in these patient populations mismatched which causes lower oxygenation of blood and higher carbon dioxide levels so dangerous to these patients.

A significant complication for patients suffering from COPD, asthma, emphysema, asthmatic bronchitis, or cystic fibrosis is the impact of the aerosolized drug administered by a metered-dosage inhaler or hand held nebulizer on the circulatory system and heart rate of the patient. Rapid heart rate in view of lower and/or poor oxygen blood levels can lead to cardiac arrthymias and/or cardiac arrest, especially in sensitive patients. However, aerosolized drugs, such as airway opener chemical compositions, typically increase heart rate and blood pressure.

The present invention compensates for such problems by metering out a smaller amount of airway opener medicines over a longer period of time for effectively attacking the airways that are in need of more time for opening up. Such airways are often the more distal and farther penetrating airways. Using smaller quantities of airway opening drugs over a greater period of time allows for greater physiological effects by freeing plugged and in spasm lower airways that are not reached by the aerosolized drugs administered by current metered-dosage inhalers and hand held nebulizers.

The inventor of the present invention, who has clinically treated patients suffering from asthma, COPD, and emphysema, such patients belonging to adult, pediatric and neonatal populations, has witnessed firsthand how cardiac rates form a barrier to further usage of airway opener treatments. Sadly, the inventor has witnessed many patients die from cardiac loss during extended treatment for dispensing airway opener drugs because such drugs did not have time to effectively reach the blocked airways. Such patients went into cardiac failure by a combination of poor blood oxygenation and increased work of breathing leading to slow suffocation from blocked airways.

The present invention combines a metered-dosage inhaler with a hand held nebulizer in one device. Moreover, the present invention uses a more efficient nozzle that dispenses smaller quantities of airway opener drugs over a longer time period, and uses canisters containing carrier gases which have calculated specific reduced densities for use as a propellant of the airway opener drugs and, in emergencies, for breathing independently from the airway opener drugs for receiving supplemental oxygen when needed. These features give the present invention the ability to achieve greater lung airway penetration allowing the airway opener drugs to reach diseased airways that current devices cannot reach.

Moreover, by including the benefits of a nebulizer in a portable device, the present invention provides better rescue abilities for individuals in severe distress who are out of hospital (such as at home and/or at work) and who are unable to timely get to a hospital or rescue center having hospital capabilities. Therefore, the present invention provides greater protection (and additional time for rescuing patients) over present devices.

By combining both a metered-dosage inhaler and a hand held nebulizer in a single device, the present invention provides greater protection for patients/users suffering from respiratory diseases and/or cardiopulmonary insufficiency so that they can stay out of emergency rooms when in crisis. Some of the many benefits of the present invention include reduced amount of hospital or emergency room visits, and more time to safely get to a hospital or emergency room for those who need to be hospitalized.

Additionally, the present invention has increased functionality over current devices by providing a patient/user with the ability to use a metered-dosage inhaler by itself or to use a metered-dosage inhaler simultaneously with a hand held nebulizer if needed. Also, the present invention provides a patient/user with the ability to simultaneously administer anesthetic drugs for the benefit of direct smooth muscle control with or without aerosolized bronchodilator drugs in refractory conditions.

Typically, helium mixed with oxygen in hospitals has a ratio of 70% helium to 30% oxygen, and may sometimes even have a ratio of 80% helium to 20% oxygen. Such composition of inhaled gas is known as heliox, and is delivered to a patient having respiratory difficulties. This composition of helium and oxygen is given for maintaining life. For example, oxygen lower than 20% cannot not be given, certainly not to those suffering from low blood oxygen already, and such high levels of helium (70% or even 80%) is used for achieving the lowest possible density for alleviating lung airway constrictions and easing the work of breathing. However, the inventor of the present invention has clinically seen the detrimental effects of using such highly reduced density gas due to the inhaled gas actually causing less gas delivery in the smallest airways where laminar gas flow is needed, and not the turbulent flows created by the highly reduced density gas. Such highly reduced density gas, together with obstructive airway diseases such as COPD, is detrimental as shown by HP law='Hagen-Poiseuille' as to further diminishing gas delivery as to the fourth power of enlarging the reduced airways.

Helium is an odorless, tasteless, non-explosive, non-combustible, and physiologically inert gas. Because helium is inert, it does not participate or interfere with any biochemical process of the body. Helium in and of itself has no curative value; it cannot support life by itself, and must always be mixed with oxygen. Helium is the second lightest gas, and does not support combustion. Helium is so light and fast that as soon as it is out of the tank it starts to separate from the oxygen. Heliox acts like oil and vinegar, as soon as you finish mixing it up and pour it out it starts to separate. Helium has a gas density of only 0.1785 g/L at standard temperature and atmospheric pressure. Breathing 100% helium can't support life and will lead to suffocation (brain anoxia); therefore, when used clinically it must always be mixed with at least 21% oxygen. When they are mixed together in a cylinder both are known as heliox.

The present invention, in addition to the above mentioned features, provides an improved lower density gas mixture. The present invention combines bronchodilating medications with airway opening drugs and anesthetic drugs into a lower density carrier gas stream for carrying such medicines and for breathing. This can dramatically reduce the work of breathing by a patient while maintaining proper velocities for the critical patient groups.

One of the goals of the present invention is not only to decrease the delivered gas density, but to also ensure that such density reductions also allowed greater flows, which are also more laminar, thus increasing the volumetric speed for each inhaled or pressurized push into the trachobronchial tree of the diseased airways of patients having breathing difficulties.

One of the main difficulties in overcoming moderate to severe airway resistance is to have breathing occur with a normal and/or near normal airflow by what is commonly sought in airflow mechanics for COPD patient populations being the attendant smooth flow of volume inhaled in the proper time, critically at the region where such laminar airflow is essential, which at the distal smaller diameter communicating airways. Such desired and sought after airway mechanics is typically missing in COPD patients, most notable during airway problem events.

The loss of laminar airflow occurs during inflammatory periods, disease, pollutants, and allergies. Laminar flow is controlled by three primary factors, one of which is currently almost entirely ignored. These three factors are (1) the diameter of the airways, (2) the density of the inspired gas, and (3) the respiratory musculature status.

The present invention unobviously impacts the first three factors, while also impacting a fourth factor, by adapting into the inventions physical principals used the pathophysiology of known COPD and airway complications seen both in adult and neonatal patient populations over the last twenty five years. COPD patients typically have some airway sequestrations due to pulmonary hyperinflation and inflammatory events as well as plugging by secretions, most occurring at the 15 to 18-22 generations of the airway bronhopulmonary tree where the diameters of the communicating airways are 1.5 mm or less. As each branching bronchiole leads down into areas termed terminal bronchioles, these progress into "respiratory bronchioles" each ending into alveolar ducts where this space becomes multiple alveolar sacs impregnated with blood via pulmonary capillaries.

The present invention achieves as a direct result of the intuitive application of the fourth factor modified to benefit greater patients usage: the fourth factor being the use of a calculated low density gas or gases in specific concentrations adapted to the airway diameters and flow mechanics clinically seen commonly and researched by this inventor in these patient populations when in moderate and/or severe airflow disturbances with blood gas data showing without such adaptations decreasing safety. The airway diameter typically at the level of the terminal bronchioles is at a 1 mm size and gets smaller into the alveolar ducts.

On average, the bronchi divide 23 times. The first 16 divisions of bronchi make up the conducting zone of the airways, in which gas is transported from and to the exterior via trachea and nasal passages. These bronchi are also called terminal bronchioles and do not participate in gas exchange. They contribute to the anatomic dead space of the respiratory system.

The present invention's use of an enlarged compressed canister of helium ("He") blended with oxygen and $N_2$, either augmented with air gas or not, is selected specifically for each patient's condition and level of disease progression. The present invention uses helium gas in concentrations at and below 55%, preferentially at 50%, whereas helium was previously delivered in concentrations at or greater than 70%. Helium in the present invention is mixed with increased oxygen concentrations to power a newer type of metered-dosage inhaler. The present invention not only has the benefits of a hand held nebulizer, but also has the convenience and portability of a metered-dosage inhaler adding increased oxygen in each mixture used for protecting the period of increased cardiopulmonary work load placed upon patients when in cardiopulmonary stresses.

Helium and oxygen concentrations augmented by nitrogen ($N_2$), is fixed and limited in the gas admixture, having a maximum concentration of 55%, and preferentially having a concentration at 50% and lower. The present invention makes usage of these mixed gases while specifically balancing and focusing on specific gas densities as relating to the Reynolds number along with increased oxygen within a specialized adaptive device being an anesthetic delivery adapter along with the present inventions design application. Thus, the present invention is more effective and achieves greater safety for the patient populations herein described by achieving optimal gas exchange to ease the work of breathing. Current devices are not adaptable for use of optimal chosen gas densities related to the current pathophysiology of a particular patient.

Helium is known for lowering the density of a gas mixture still has a higher and exceeds the velocity of air, having a higher density. This limits the flow of the mixed gases, especially in regions of the lung where laminar flow predominates, thus causing increased Ventilation/perfusion (V/Q) mismatching. Adding the further hypercapnic i.e., elevated carbon dioxide blood levels resulting from complication events. Being the attendant hypoxic conditions and its increased demands physiologically now placed upon patients during periods such typical of these patient population's during exacerbations. The present invention uses a unique storage and dispensing means of self contained envelopes of anesthetic gases either in liquid or frozen form to further dilate the communicating airways when inflamed and spasmodic as refractory state.

To maintain the optimum nearest density while using the safest level of effective $N_2$, the $N_2$ percent concentration will be static at all levels of heliox mixtures at 30%, and air at 10% varying helium and oxygen percentages with a maximum oxygen percentage of 40% and a maximum helium percentage at 55%. A key feature of the present invention lies in keeping the inhaled gas density at or slightly below the density of air for both ease of entry and optimal flow by maintaining laminar flow into the smallest bronchioles feeding the air sacs of the lungs being at and past the terminal bronchioles.

Below are example gas mixtures suitable for use with the present invention. In determining the density of the below gas mixtures, as seen herein below, the masses of the gases were added together to determine the combined mass of the mixture (e.g., mixture mass=mass of x+mass of y . . . ) Then, the combined mass of the gas mixture was divided by the volume of each gas with its specific concentration within the mixture to determine the density of the mixture in the container: d avg.=average density of said mixture.

Pressurized canister gas mixtures for supplying aerosol drug and/or for breathing alone:

Example 1. % of He is 28% (0.280×0.178)+% of $O_2$ is 23% (0.230×1.43)+% of $N_2$ is 30% (0.300×1.25)+19% air (0.19×1.29 g/l)
He=0.049+$O_2$=0.3289+$N_2$=0.375+Air=0.245=d avg.=0.9979 g/l Example 2. % of He is 30% (0.300×0.178)+% of $O_2$ is 25% (0.250×1.43)+% of $N_2$ is 30% (0.300×1.25)+15% air (0.15×1.29)=d avg.

He=0.053+0.3575+0.375+0.193=d avg.=0.9875 g/l

Example 3. % of He is 30% (0.30×0.178)+% of $O_2$ is 40% (0.40×1.43)+% of $N_2$ is 25% (0.25×1.25)+5% air (0.05×1.29)=d avg.

He=0.0534+$O_2$=0.572+$N_2$=0.3125+Air=0.0645=d avg.=1.108 g/l

Example 4. % of He is 20% (0.02×0.178)+% of $O_2$ is 30% (0.30×1.43)+% of $N_2$ is 40% (0.40×1.25)+10% air (0.10×1.29)=d avg.

He=0.0356+$O_2$=0.429+$N_2$=0.5+air=0.129=d avg.=1.0936 g/l

Example 5. % He is 35% (0.350×0.178)+% $O_2$ is 35% (0.350×1.43)+% of $N_2$ is 20% (0.20×1.25)+10% air (0.10×1.29)=d avg.

He=0.062+$O_2$=0.501+$N_2$=0.25+air=0.129=d avg.=0.942 g/l

Example 6. % He is 55% (0.55×0.178)+% $O_2$ is 25% (0.25×1.43)+% $N_2$ is 10% (0.10×1.25)+10% air (0.100×1.29)=d avg.

He=0.098+$O_2$=0.357+$N_2$=0.125+air=0.129=d avg.=0.709 g/l

Historically, using a very low density gas mixture having a high concentration of helium (e.g., 80%) and a much lower concentration of oxygen (e.g., 20%) would allow easy gas entry (its density would be 0.427 g/l). However, such a gas mixture would have a Reynolds number (Re) too high for effective laminar flow due to its high velocity entering the wide upper airways, greatest trans airway pressure, which at the lower conducting airways due to the HP equation such ¼ airway sizes increases resistance at the $16^{th}$ power causing turbulence with its increased back pressure. This causes increased boundary layers prior to entry into the terminal bronchioles and causes by such back pressure an increase in mismatching of volume to perfusion in the air sacs of the lungs. Not only will inspiration time need to be elevated, but exhalation time suffers. In this patient population, inspiration to expiration time is typically 1:4 and longer (1:5, 1:6 . . . etc.) by reducing the amount of aerosol transport volume in the lower conducting airways. The present invention has the benefit of achieving greater filling in dead space allowing greater volume exchange for oxygen and $CO_2$ waste gas transfers. The present invention's adaptations and benefits allow increased transported volume with less turbulence having less back pressure to further limit gas volume delivery and therefore achieves more laminar flow for the same pressure influencing said flow.

For instance, atmospheric air contains approximately 21% oxygen, and 78% nitrogen ($N_2$), and a few other trace gases. Atmospheric air has a density of 1.29 g/L. The density of a gas equals the total gram molecular weight divided by its universal molar mass of 22.4 liters. As an example, oxygen has a molecular weight of 16. Since there are 2 molecules ($O_2$) the total gram molecular weight is 32. Therefore, the density is 1.428 g/L, approximately 1.43 g/l, (32/22.4). Helium has a gram molecular weight of only 4, so its density is 0.178 g/L. To calculate the density of heliox, simply multiply the percentage of the gases, add together and divide by 22.4. As an example, 80% He and 20% $O_2$:

$$\frac{(.80\times 4)+(.20\times 32)}{22.4}=\frac{3.2+6.4}{22.4}=\frac{9.6}{22.4}=\underset{\text{(rounded up)}}{.4285\text{ g/L}}$$

molar mass $N_2$=44.0128 g/mol/22.4=1.96 yet as STP had at 1.25 g/l.

As mentioned above, atmospheric air has a density of 1.29 g/L.

As such, prior art considering foremost the lowest density mixture to specifically achieve ease of work of breathing during typical labored periods of breathing disregards the increased V/Q inequalities resulting from such lowered gas densities. This in fact nullifies the benefits of the lower density achieved by the mixture and actually causes deleterious effects to the patient using such mixture.

As such, prior art considering foremost the lowest density mixture to specifically achieve ease of work of breathing during typical labored periods of breathing disregards the increased V/Q inequalities resulting from such lowered gas densities. This nullifies the benefits of the lower density gas mixture and actually creates negative effects for the patient inhaling such lower density gas mixture.

An embodiment of the present invention uses a lowered heliox (e.g., helium oxygen mixture) concentration then previously used or even considered along with its usage as a carrier gas propellant along with $N_2$ to achieve a greater effectiveness. Achieved by matching the current clinically known pathological conditions presented by both lowering the velocity of the mixture inhaled; altering the labored breathing pattern to a more compliant volume to pressure ratio, this by assuaging the dyspnea which is clinically known to increase both rate of breathing and poor lung chest wall compliances.

By lowering the heliox mixture's density too much, as for example heliox having ratios of helium to oxygen of 70/30 and 80/20, cause velocity turbulence as when the Reynolds number is approached or exceeded, typically below 1500 and less. This prevents the more distal penetration of both volume of fresh gas and medicine to the lower smaller diameter airways and leads to mismatching of the V/Q ratios. Thus, both normal usages of air oxygen mixtures sans helium and previous heliox gas mixtures have proven largely ineffective, due primarily to increasing the target of lowering the inhaled gas density without bypassing the relevancy of the increased velocity thus achieved of the prior art heliox mixtures of 70% helium and higher while failing to compensate for the oxygen concentration, keeping it fixed at either 30% or 20%. This results in limiting the exchange volume of fresh gas affected dysfunctional areas of the lung fields. Most especially when used in the concentrations as heliox normally used as 80% helium to 20% oxygen, or 70% helium to 30% oxygen in prior art devices.

The adaptation of lower density gas mixture powering the portable inhaler is reserved in keeping the gas mixture density to such a point that the gas mixture both delivered and powering the present invention are not contributory to the acceleration which would cause turbulence at more distal communicating airways having diameters less than 1.5 mm that lead into terminal bronchioles. This is had by keeping the gas mixture below a Reynolds number of 1200.

The Reynolds number (Re) is a ratio that expresses itself in a dimensionless unit where flow either within air or water or another liquid is calculated to be below “1500” as this number relates to flow turbulence, while flow below 1200 expresses a laminar flow. Such laminar flow is required for COPD diseased states for preventing both increased $CO_2$ waste gas and lower oxygenation of blood in patients.

The ratio of Reynolds number (Re) is obtained by having the inertial force over the viscosity force. When an object (e.g., aerosol, carrier gas, etc.), in the case of the present invention a gas mixture or single gas used to carry the airway opener drug and to supplement the breathing of the patient, interacts with a fluid, there are two forces to be accounted for: one is the inertial force and the other is viscosity. An important part of the Re is the diameter of the channel, the smaller communicating airways or its length, which here the length is very negligible in such calculations.

In prior devices, low density gases achieved by higher helium/oxygen concentrations (e.g., having helium to oxygen ratios of 70/30 or 80/20) while made available, but not surprisingly, did not achieve such benefits as those sought or theorized. The reason was V/Q inequalities adding further hypoxia and hypercapnic episodes to this patient population during bouts of infection, and airway spasms both with and without airway plugging, leading to increased usage of drugs and or; usually both ventilatory management. The reasons were confusing for clinicians because the lower density meant greater ease of work of breathing when using higher helium concentrations, typically 70% and often 80% helium, mixed with 30% or 20% oxygen, respectively as this provided greater volumetric delivery of fresh gas to the lungs via its communicating airways.

The issue neglected, however, was that the volume delivery of fresh gases is required to be in the easiest acceptable form: that of a laminar gas flow in the smaller diameter communicating airways. Here, airflow is primarily conceptualized by the inventor by laminar flow, not bulk turbulent flow negatively affecting gas delivery such that areas not ventilated are silent to gas exchange and fresh gas is lacking to replace that which was just used in the prior breath, now such distal smaller communicating airways being sequestered by both disease and infections and/or plugging, and/or components of all three or any combination of the said two, inhibit the fresh gases entry. Such sequestrations of said communicating airways are by pulmonary hyperinflation in addition to the intimae of the communicating airways diameter reductions, all leading to increased V/Q mismatching and less effective gas exchange.

However, when helium is modified in its reduction of the total gaseous delivered density adjusting such mixtures to approach a density near that of air at 1.29 g/l the acceleration of the delivered gas is reduced and the Reynolds number (Re) is less allowing for a more laminar flow and as such an increased gas delivery in the smaller distal reduced diameter communicating airways. This increases V/Q matching and increases oxygenation and waste gas (CO2) removal.

Therefore when nitrogen (of the inhaled air) is replaced by helium, airway resistance is reduced due to the lower density of the inhaled gas. This means that when one breathes heliox, airway resistance is lowered, thereby requiring less mechanical energy to ventilate the lungs, or the “Work of Breathing” (WOB). This is seen primarily at the mouth, nose and major conducting airways where the diameter is above 4 to 6 mm, but not at levels below 2 mm to 1.5 mm, providing the level of helium does not exceed the point at which viscosity detrimentally affecting the flow characteristics of the patient by causing V/Q mismatching.

As a further example of such viscosity effects, it is known that heliox has a higher viscosity which affects the laminar in infants who have bronchiolitis. Laminar flow is the predominant flow in the peripheral airways or bronchioles. Therefore, patients with true bronchiolitis, where the inflammation and obstruction is in the peripheral airways, will have decreased flow with heliox and increased work of breathing.

Issues that needed addressing in the present invention for a self-use portable device for inhalation of anesthetic mixed gases included the maintenance of the swallow, gag, and cough reflex in chronic lung conditions where a tussive effect is critical to the maintenance of clearing ones airways. Thus, such reduced MAC was designed. Another issue was simultaneously avoiding combustion and explosion while maintaining the proper flow rate of the anesthetic gas being inhaled with safety. A further consideration was that during treatment via nebulizer techniques the patient has motor control and proprioceptive self-awareness.

Another issue addressed by the present invention is that known nebulizers, requiring oxygen to supplement the treatment, use large metal gas tanks connected to an oxygen line for supplying oxygen to a patient. Therefore, known nebulizers for supplying oxygen are not portable. In contrast, the present invention reduces the size of the gas tank to a small canister that can be screwed into the bottom of the portable rescue inhaler. The present invention is able to reduce the large metal tank of known nebulizers to the size of a small canister by providing less pressure and a different mixture of gases (in particular, less helium) in the canister than currently done. The small canister is replaceable, meaning that it can be replaced with another canister having either the same concentration of gases or a different concentration of gases depending on the patient’s needs. In one embodiment, a canister has 3-4 days’ worth of at minimum intermittent usage.

Another problem solved by the present invention is the problem of tachypnea and distended lungs causing $CO_2$ retention and frequency dependent non-compliant lungs. The present invention solves this problem by allowing for more laminar flow at distal and peripheral airways via the diminished viscosity of the chosen heliox levels and the option of adding anesthesia to alleviate the anxiety of patients experiencing dyspnea, meaning a feeling of air hunger. The present invention uses lower density and lower viscosity gas mixtures as a carrier gas for further depth and penetration by an aerosol medicine. The present invention blends lower density heliox gas with a lowered MAC of an anesthetic for inhalation by a patient.

The present invention uses a combination of gases having a more efficient density reduction which is not too large so that the velocity of the gases does not cause turbulence at and near the smaller lung airways. Such turbulence prevents the smaller airways from getting ventilated which in turn prevents the smaller airways from receiving the medicine that is dispensed to open them up over time. This causes increased V/Q mismatching and increased shunting of the blood. The present invention utilizes a mixture of carrier gases that dispense smaller quantities of airway opening drugs over time together with carrier gas streams having a modified slightly reduced density, and the ability to inculcate anesthetic gas within the aerosol carrying such drugs. The present invention allows airway opening drugs to achieve greater penetration by traveling further into the lung airways despite airway spasms and inflammation thereby reaching diseased airways that medicine dispensed by current devices cannot reach.

A diminution in communication airway diameter, those leading to the actual air exchange regions within the lungs is a major cause in restrictions to air flow, and if crossing the time required in delivering that flow; which is flow per time delivered is in fact equal to a volume moved, as such that is the tidal volume entering ones airways and further down delivered to ones air spaces. Such relationship, of airway resistance is a direct function of airway diameter. This relationship has been found and cited in the literature to be the inverse power of a forth level, as dictated by the Henry Pousielle, H.P.law in standard fluid dynamics notation is revealing of such airway to diameter as air flow resistance relationship by the following. In physics notation $$\Delta P = \frac{8\mu LQ}{\pi r^4} \text{ or } \Delta P = \frac{128\mu LQ}{\pi d^4}$$

Here the ΔP is the pressure drop. L is the length of pipe, μ is the dynamic viscosity. In this system L=the axial length of the air-tube under consideration, "d" its diameter Q is the volumetric flow rate, r is the radius, d is the diameter, it is the mathematical constant (approximately 3.141592654).

Thus, by that equation, the present invention has two mechanisms allowing the ability to affect a direct functional relationship between airway diameter and resistance to flow/time which previous devices effect assuming the same viscosity of the fluid medium. Thus, an improvement over previous devices is that we now can alter that viscosity as well as the airway diameters adding a third and fourth benefit of the present invention unmet in previous devices.

Which for many patients in crisis as breathing air with oxygen increased in inhaled concentrations has a greater density is obviously proportionally greater.

However, by inverting this statement—to make the invention's point, if we can diminish the density of the medium (density of room air) traveling through the pipe ("L"=communicating airways) here that would mean 1. Diminishing the viscosity of the gases flowing through the air tube by use a calculated in the preferred embodiment, a premixed helium, oxygen air mixture. As well as 2. Altering the actual diameter "d" as well as the radius, "r" we would achieve a synergistic effect greater than prior art has accomplished.

Still the variables include the Reynolds number (Re); Smooth flow called "Laminar flow" through a non branched "linear" (straight) tube is described by the Hagen-Poiseuille equation: $\delta P=RV=8L\mu/\pi r^4$, where δP is the change in pressure, R is the resistance, V is the gas flow rate, L is the length of the tube, and r is the radius.

When flow of a given gas mixture exceeds a critical velocity, the flow becomes turbulent and the flow equation changes to $\delta P=V^2 \rho f L/4\pi^2 r^5$ where f is frictional factor. As the viscosity of the mixed gas inhaled by a patient/user increases, laminar flow is disturbed, being that laminar flow is the predominant flow in the peripheral airways or bronchioles the viscosity impacts negatively on the lower density gas mixtures.

Reynolds number (Re=ρUd/μ, where ρ is the gas density, U is the velocity, d is the diameter of the tube, and μ is the viscosity of the gas) predicts whether flow through a non-branched "straight tube" will be laminar or turbulent. When the Reynolds number in a straight, unbranched tube is greater than 1500-2000 units, turbulent flow occurs. In a branching tube or around an obstructed region, turbulent flow occurs at a lower Reynolds number. Note that laminar flow is directly dependent on the gas viscosity μ, whereas turbulent flow is directly dependent on the gas density ρ.

In the present invention, the Reynolds number (Re) expresses the ratio of inertial (resistant to change or motion) forces to viscous (heavy and gluey) forces. From a detailed analysis of the momentum conservation equation, the inertial forces are characterized by the product of the density r times the velocity V times the gradient of the velocity dV/dx. The viscous forces are characterized by the dynamic viscosity coefficient mu times the second gradient of the velocity d^2V/dx^2. The Reynolds number Re then becomes:

$$Re=(r*V*dV/dx)/(mu*d^2V/dx^2)$$

The gradient of the velocity is proportional to the velocity divided by a length scale L. Similarly, the second derivative of the velocity is proportional to the velocity divided by the square of the length scale. Then:

$$Re=(r*V*V/L)/(mu*V/L^2)$$

$$Re=(r*V*L)/mu$$

the Reynolds number can be further simplified if we use the kinematic viscosity nu that is equal to the dynamic viscosity divided by the density. As such by the HP law in conceptual awareness of the physic laws in such communicating airways and in such pathology as clinically found in COPD patient populations then, $\Delta P=r^4/v$. This equation shows:
1. If the flow is halved, the resistance would be halved and the required pressure gradient would be greatly reduced.
2. If the flow rate remains constant, the pressure will vary inversely by the fourth power of the radius (in other words, for each unit of measure smaller the radius of the tube is, the pressure required to move the same amount of air through this smaller tube increases exponentially).
3. If the radius is reduced by half, resistance would be increased sixteen times. As seen in semi collapsed communicating airways as found in the peripheral most distal airways proximal to the lungs actual air sacs where gas exchange in fact occurs.

Or, if reasoned via combined equations, we have, nu=mu/r->Re=V*L/nu->Re=pVD/u, where p=density, V=velocity, and D=diameter.

In the lungs there are variables which cause fairly involved fluctuations in the velocity, especially considering the amount of air taken inspired at the time as well as pressure changes in the pull of initial inspiration. Along with the condition of the lung to chest wall compliance at the time of calculations obviously, dependent upon the condition of the patient at time of calculations. The density of the mixture is previously calculated, the airways diameter concerned with here is less than 1 mm and that is consistent in the conducting airways at the level concerned with mass and transient flow immediately prior to the terminal bronchioles. The viscosity of the gases is consistent along with its admixture used as such using the data we have.

Helium's density is less than nitrogen's so at any given gas flow there is less turbulence. This property of helium can benefit patients with airway obstructions by improving gas exchange, lowering airway resistance, and reducing work of breathing providing the viscosity is not increased to where the V/Q mismatching detrimentally effects the patients.

With helium, the oxygen percentage was often at concentrations of room air 20.9%, rarely higher. This generated a low gases density mixture with oxygen for breathing and attempts at removing the work of breathing by those who had either airway diameter reductions, caused by diseases of the airways, like COPD, spasms in asthma, inflammations, allergies, aspiration pneumonitis, pre, during and post-endoscopic-procedures for clear viewing and aspiration of material effecting airway diameter reductions, as well as invasive surgical interventions.

Therefore when nitrogen (of air) is replaced by helium, airway resistance is reduced due to the lower density of the inspired gas. This means that when one breathes heliox, airway resistance is lowered, thereby requiring less mechanical energy to ventilate the lungs, or the "Work of Breathing" (WOB). Again this is providing the level of helium does not exceed the point at which viscosity detrimentally affecting the flow characteristics of the patient by causing V/Q mismatching.

Heliox is utilized to alleviate conditions that decrease airway diameters with its concomitant increase in work of breathing to overcome the diminished flow rate encountering higher airway resistance to air flow. This is also found in pediatric populations as in respiratory insufficiency of the newborn period, croup, and further down the airways as in bronchiolitis.

In order to increase the efficiency and ease the work of breathing in obstructive airway activity, while simultaneously inhaling increased oxygen concentrations; this to protect the cardiopulmonary components, heart work load under broncho-constrictive periods and or increased workload of breathing air and onto further deteriorated levels where actual diminished oxygen content of blood occurs with both prior symptoms. Such during the initiation and during the dropping of blood oxygen levels, the inventions multiple abilities allow for greater yet safe oxygen delivery, as such Oxygen levels are increased along is the increase in the helium concentration, both must be interrelated this due to density and oxygen wash out of the alveolar system within COPD dependent lung fields, which historically may lead quickly to a respiratory depression along with hypoxemia which is extremely and known to be dangerous and typically allowed by current modes of unsafe oxygen usage with HHN and physician and unaware professional treating this patient population. As such the invention is greater than prior art by including not only its abilities of oxygen enrichment while compensating for gas density by limiting the helium in conjunction with oxygen increments of percentage delivered and as such inhaled. Used as a preferred yet limited ratio range in both quantity, and percentages used.

In one embodiment of this invention, there is a canister having heliox combined with $N_2$ in lower percentages with an additional option to utilize added anesthetic gas as a vaporized gas. If selected, an anesthetic gas combined with oxygen gas allows for the pressurized drug in aerosol form to be delivered with optimal bronchodilator effects. This achieves greater and safer airway opening for users/patients having diseases affecting airway diameters and helps to reduce the increased work of breathing. These benefits are not achieved by current devices.

The remaining gas may be either nitrogen and/or any of the safe inhalable inert gases preferred in anesthetics where excess nitrogen would cause $N_2O$ to be produced itself in quantities above 85% this to protect against breathing radical gases and combining with halogens as compounds formed with halogens and certain organic compounds which are dangerous, and can be explosive.

Additionally, utilizing high oxygen levels; the invention is describing here a preferred embodiment and the inventor states, that the invention is not limited to the stated ratios described herein of the oxygen gas utilized, but is chosen as the preferred embodiment. As such if and when oxygen concentrations are used above 50% for extended periods external nitrogen in the ambient air as supplemental additional $N_2$ gas inhaled during treatment; the patient may breath outside the devices mouthpiece or supplemental mask during therapy and flood the airways with a nitrogen level per breath, this in preventing absorption atelectasis due to the washout of nitrogen filler gas within the terminal branched lungs alveoli. The inventions preferred embodiment being with several carefully chosen pre-selected concentrations of four differing oxygen levels premixed to their concentrations with the helium in the ratios stated herein. Being $O_2$ contents of 23%, 25%, 30%, 35%, and 40% will be combined with helium and nitrogen in any of the six stated ratios given herein. These ratios were carefully picked for easing of the work of breathing, cardiopulmonary increased condition, selected as well for the prevention of washout-atelectasis, the highest usage for safety and least costs of helium use.

While in hospitals the usage of less than 58-60% Helium is considered less than beneficial, this primarily on ventilators in pediatric usages, this due to the density of the gas. The invention in its utilization of the combined benefits of reduced gas velocities while simultaneously having lowered density achieves a greater oxygenation blood level along with increased bronchodilator effects. Further allowing when called for anesthetic gases creates a greater effect and a greater list of advantages for the dimunition in both the work of breathing, bronchospastic airway conditions that clinically are often seen clinically refractory status necessitating being placed upon a ventilator. As seen in prior art lacking the present inventions trifold advantages and physiological benefits therein obtained. Equally with the present invention greater cardiac protective measures are realized, with greater reduced costs.

The invention can achieve a greater ease of breathing and greater depth of aerosol penetration with the usage of bronchodilator or steroid or antibiotic therapy agents. Additionally, a helium oxygen mixture is still less dense than room air without the helium to lower the density of the gases inhaled due to the use of increased oxygen usage The invention does not limit the usage to the stated gases herein or the percentages for usage in the teaching of this invention. These are the preferred embodiment for the inventions portable anesthetic inhaler and for the maximum safety. The inventor states that such concentrations and ratios may be altered to achieve higher and lower values as applicable for both portable inhaler usages and for emergency ventilator usages in another embodiment to be stated herein later. And as such the invention is not limited to the stated preferred embodiment as given herein.

As designed the invention utilizes a hereto un-described technique for portable and non-portable anesthetic usage, said technique and usage allows for a greater ease of application, being of greater safer and more economical for patient usage both in the field and the hospital, said means being a quantity of anesthetic liquid as a reduced concentration as percentage typically below 35% of the known and documented concentration achieving a given MAC (Minimum Alveolar Concentration) for that specific agent, and at 18% below the typical combined MAC for combined agents when used in conjunction, is placed within a wax and or sugar or similarly non-toxic material to function as an "anesthetic envelope."

Said 'anesthetic envelope,' which upon heating melts enough of said material away to release a contained therein said wax and or sugar anesthetic envelope a defined liquid quantity of anesthetic gas. Further several compartments may each be well defined within said anesthetic envelope, each having a compartment, each compartment having a differing quantity of wax and or sugar and or similar material which upon heating melts away allowing a defined quantity of anesthetic(s) to be released as a gas, either one after the other as anesthetic gas of differing types; $N_2$, then Isoflurothane, etc. . . . , or in sequence. Or designed to be released after a defined period this due to the heat applied to the varying differing vapor and atmospheric pressures an low boiling points that differing anesthetics are known to have.

The compartment is heated by a set of wires contained within a small compartment which receives said anesthetic envelope. Said wires get the energy to heat up by a battery either disposable or non-disposable. The wax and or sugar envelope material is after usage ejected out to the compartment and another fresh envelope is inserted either by a hand pressed mechanism or spring loaded mechanism that directly feeds said compartment with said anesthetic envelopes. The compartment is bleed directly with the pressurized gas mixture that is reselected as heliox, this as many anesthetic gases are three to ten times the know density of air. As such, the low density heliox allows a greater deposition upon both the weakened inhalation of the ill and aggravated COPD patient.

Nitrogen ($N_2$) is a colorless, odorless and tasteless gas that makes up 78.09% (by volume) of the air we breathe. It is nonflammable and it will not support combustion.

Nitrogen gas slightly lighter than air and slightly soluble in water, commonly thought of and used as an inert gas; but it is not truly inert. It forms nitric oxide and nitrogen dioxide with oxygen, ammonia with hydrogen, and nitrogen sulfide with sulfur. Nitrogen compounds are formed naturally through biological activity. Compounds are also formed at high temperature or at moderate temperature with the aid of catalysts. At high temperatures, nitrogen will combine with active metals, such as lithium, magnesium and titanium to form nitrides. Nitrogen is necessary for various biological processes, and is used as a fertilizer, usually in the form of ammonia or ammonia-based compounds. Compounds formed with halogens and certain organic compounds can be explosive.

Use of the invention is additionally conceptualized as combined with a densitometer control-in-line with the oxygen concentration control incorporated within ventilators. This is for modifying the density of the inhaled and exhaled gases during ventilatory care and support.

Obviously the density of a gas is affected by the atmospheric pressure the gas is subjected to, but in one and herein the preferred embodiment it is calculated at the existing atmospheric level the population is exposed to, being slightly modified at sea level herein New York City, USA then in the Grand Canyon Wyoming. For example PV=mRT, D=m/v, so D=P/RT.

This for D=Density, R=Gas Constant (8.314), T=Temperature (Assume 273K)., for Oxygen, R=R0*M, where M=32 and R0 is 8.314., M is molar mass of 02=32 g/mol., R0=Universal Gas Constant so R=8.314*32=266.048., D=130000/266.048*273

D=130000/72631.104., D=1.79 g/L.

This as opposed to oxygen's density at atmosphere of 760 torr=1.43 g/L. Would be Molar mass of O2=32 g/mol. pressure=742/760=0.976 atm. T=24+273=297 K. As such the density of oxygen at 24 degree Celsius and 742 torr.::: d=molar mass×p/RT=32×0.976/0.08206×297=1.28 g/L.

Air's density is 1.18 at room temperature; as affected by temperature and pressure for ease of relationship "air" has a mean density of 1.29 g/L.

Finally, density does in fact change with temperature and atmosphere. Fortunately, such changes in both temperature and atmosphere are limited at sea level and environmental values.

As a comparison, dry air has a density of 1.225 $kg/m^3$, wherein the density of oxygen at 25 degrees Celsius is 1.429 $kg/m^3$, the density of nitrogen at 25 degrees Celsius is 1.2506 $kg/m^3$, and the density of helium at 25 degrees Celsius is 0.1787 $kg/m^3$.

As clearly seen, helium is roughly seven times lighter than air. It is imperative to utilize a reduction in gas density to affect a lower inhaled gas density to prevent greater V/Q mismatching in patients suffering from COPD and to allow for easier breathing which affects the flow characteristics of the moving gas stream. Gas density affects the velocities of gas through airways most essential during times of breathlessness and low cardiac reserve. However, this must be below a critical threshold. Although current knowledge varies as to such threshold level, research has found that gas mixtures containing 80% helium causes less volume transmittal in the distal lung fields post the terminal bronchioles. Therefore, the concentration of helium in this invention is always below this number by a minimum of 25%, thus no helium is given above 55%, whether mixed with oxygen or not. Higher oxygen concentrations negatively impact upon the benefit of the application of heliox usages, this due to the increased molecular weight of the oxygen. As in the heliox mixture, the higher the oxygen concentration, the greater the density becomes because of the added gram molecular weight. Also, the present invention compensates for greater cardiac support and ease of muscle usage in increased work of breathing by adding supplemental oxygen to the mixture inhaled.

In respiratory physiology increasing the individuals airway diameter, means decreasing the inflammation and the constriction, each a variable independent of the other yet in a dynamic system as the respiratory one, both relate one to the other and as such influence one another. A greater inflammation affects a larger diminution in radius of the air tube involved. Inflammation can be reduced by cooling; use of anti-inflammatory agents, e.g. Steroid, anti-histamine's locally applied, and reduction of pressure trauma to the involved site. For hospitalized and patients outside the hospital who are near or in airway obstructive and or restrictive crises in addition to regular inhaled use of B-adrenergic agonists for bronchodilator therapy, treatment should be augmented with substantial doses of systemic glucorticoids. Most physicians recommend 30 to 120 mg of methylprednisolone i.v. every six hours.

Anti-histaminics locally applied have some value, but are largely impractical as they may be unfeasible. Steroids are the more reliable mechanism, but they take time to cause an anti-inflammatory response, cooling carries with it the antagonistic effect as time of causing, this for an unresponsive bronchoconstriction. Thus, steroid therapy may work well over time, but if not caught timely may well be too late.

The present invention is an improvement over prior devices by having a single portable device able to utilize both techniques, i.e. lowering the breathing gas mixture density via use of selected heliox mixtures and applying an airway opener rescue drug in such low density carrier gas stream. This achieves first and foremost a combinational effect of low density gas reaching farther and more obstructive airways, where air or air oxygen combinations at the stated density would be unable to reach, while simultaneously increasing the airway diameter of the user/patient.

Such increased diameter combined with a low density gas, making the patient/users work of breathing less and getting more volume for each negative inspiratory pull. Such direct effect of achieving a further benefit of reaching distal airways; the communicating airways are similar to an inverted tree its branches may be thought of as airways. Said airways are much smaller upon each distal division; distal from the mouth downward into the lungs five independent lobes. Said smaller branches of communicating airways that are much sooner and become partially plugged with inflammatory material and un-cleared mucus. Further complicated and sequestered by spasms. Now by the carrier gas carrying such airway opener drugs further into the smaller airways. This via application of a "three tiered synergistic technique" our invention is designed and achieves.

The invention's "third tiered technique" embodiment uses several specific chosen gas densities limiting the velocity to affected dysfunctional lung regions commonly seen in both COPD patients and cardiac compromised COPD patients, said concentrations are used as described herein.

Additionally, the present invention also conceptualizes the use of a modified densitometer in line with a heliox reservoir connected to a control that monitors both pressure and oxygen concentration as well as helium concentration, thus providing the ability to adjust the ventilator to compensate for the patient's breathing during critically ill periods. As such, the present invention is an improvement over prior ventilatory and/or supportive and/or mandatory ventilation devices in the field of respiratory therapeutics. Again, the inventor states this is not the only preferred embodiment for the portable metered-dosage inhaler and anesthesia device of the claimed invention.

Being that of the use of an anesthetic gas along with low density gases with higher oxygen concentrations powering the airway opener drug as an aerosol, this to increase the usually diminished FRC and increased CO2 retention due to such anesthesia use via inhalation. As a separate compartment but in conjunction with the main airflow conduit a section with means to contain, insert and eject a packet of wax, or sugar coated non-irritating envelope and or miniature cylinder containing such mixed anesthetic gas(s) undesired proportion.

Said wax and or sugar that upon heating dissolves enough to allow its internal liquid anesthetic to escape into a flow chamber where fresh gas and selected gas is channeled affecting a flow over vaporized anesthetic is realized. Said anesthetic become available for inhalation only upon activating the heating element within the drawer where the encased sugar or wax coated envelope houses an anesthetic liquid which upon heating by a powering tray, said powering tray receiving current from a disposable battery. The heating that is applied melting said sugar and or wax coat to releases the anesthetic as inhaled gas to flow within the gas aerosol conduit, which is also moved by negative pressure via the inhaled action of the user/patient/person. Said anesthetic envelope is housed within a foil container within a compartment with means for inserting and ejecting the used anesthetic.

Fresh gas flow from the container pressurized cartridge enters the inlet of the anesthesia vaporizer which is turned on by safety switch and release of a safety lock. The concentration of anesthesia is preset the volume is variable depending on if the patient uses one or two envelopes containing the preset concentration of anesthesia and the carrier gas (also called chamber flow, which flows over the liquid agent).

Awareness of laminar flow in the peripheral airways is often neglected as to the driving pressure and the distension of the hyperinflated lungs. As such, the invention's use of lower heliox concentrations has not been previously used in the field of respiratory therapeutics which typically use 80% helium and 20% oxygen, or commonly 70% helium and 30% oxygen for dispensing inhaled gases having a density of just 0.552 g/l causing greater velocities which cause increased flow turbulences as explained in detail above.

The invention can achieve the benefit of increasing the depth of breathing and simultaneously the reduction of $CO_2$ retention in obstructive type COPD patients, resulting in a greater decrease in the respiratory rate of COPD patients. And in less compressive effects upon the lungs FRC and thus an increase in the oxygenation of the blood with a concomitant reduction in CO2 retention on ventilator supported patients as well as spontaneously breathing patients.

The invention is both a flow over and temperature compensated device and is portable. "Flow over" in the fact that the carrier gas and or gases chosen for density moderation flows over the surface of the liquid volatile agent in the vaporizing chamber, as opposed to bubbling up through it (as example the common older usage of "the copper kettle" and newer Vernitrol). "Temperature compensated," in that the device is equipped with automatic devices that ensure steady vaporizer output over a wide range of ambient temperatures, with an automatic shunt bypass within the powering heating tray; where the anesthetic envelope sits, this to disconnect the current power to the powering heating tray should anesthetic be used up in shorter period of time. Anti-tipping feature of the device is ensured by the trays depth and surrounding shield to prevent anesthesia leakage during heating and vaporization.

The reason for such application of anesthesia to breathing difficulties as found in COPD and asthma is of two main issues. First the inflammation often attendant with airway spasms and second the increased spasm caused by the underlying inflammation, which is largely unaffected by hand held nebulizer and nebulizer drugs combating muscular spasmodic irritation. Both further complicated by the fact that higher gas carrier streams holding aerosolized medicine within such streams are typically deposited by a case of inertial impaction, meaning each divisional, generation of tracheobronchial tree, alternation within the airways when an aerosol is carried within such stream of higher gas density impacts out onto the bronchial mucosa at the angle of change the air stream is carrying such particles within. For in certain lower communicating airways airflow does not move by only bulk flow, meaning the airflow is effected by molecular collisions and partial pressure gradients into the distal air sacs. It is at these points that airway plugging and shunting of blood flow to more aerated branches of the communicating airways occurs. As such, use of a combined lower density gas mixed with anesthesia can achieve more effective rescue of a patient experiencing respiratory insufficiency bordering on ventilatory failure and having the need to be intubated and placed onto a ventilator.

These applications provide the health care provider and individual user with unparalleled control to assist their deleterious airways conditions. This is a significant improvement over previous devices.

The purpose of conscious sedation via the reduced 18 to 35% of MAC for a full three to eight minutes is to produce a state of relaxation and/or pain relief allowing for a greater, deeper breath and for a greater aerosol penetration. This can achieve a greater depth and coverage throughout the respiratory tracheobronchial tree by using anesthetic gas(es) along with either bronchodilator therapy and/or heliox as an aerosol gas carrier.

The invention does not exclude the usage of benzodiazepine-type and narcotic medications, to facilitate performing a procedure such as a biopsy, radiologic imaging study, endoscopic procedure, radiation therapy, or bone marrow aspiration for portable usage at bedside or in the field or at home.

We can thus reduce the pressure to drive such fluid across and though such pipe (airway). Reduce the work of breathing. That is precisely the reason we use specific mixes of helium to oxygen, guided by the persons present status, i.e., cardiac debilated, verses a normal healthy individual with good cardiopulmonary status.

While oxygen alone reduces breathlessness associated with activity, heliox reduces resistance in the lungs during exhalation which allows COPD patients to exhale more air. This means the air sac's within the individual's lungs will be better able to eliminate carbon dioxide from the body.

One of the invention's goals is to provide control over treatment for the patient's benefit for alleviating the patient's diseased airways and treating airway spasms and/or allergic conditions which are not stable causing the patient's airways to lose their naturally sustained diameter.

Thus, our device achieves a reduction both in the viscosity of the inhaled carrier gas to stabilize and increase the airway diameter to achieve more laminar flow and thus a greater flow rate/time for the benefit of the individual and or patients benefit as measured in standard tidal volume, FEV1-3 and VC measurements as L/sec flow rate.

Controlling Inspired Fraction of Agent, $F_I$ $F_I$ depends on total fresh gas flow (FGF in L/min), total volume of the breathing system or circuit, and any absorption of agent by the anesthesia machine and breathing system.

Factors Affecting Alveolar Fraction of Agent, $F_A$ $F_A$ depends on three variables: uptake of agent from the lung, pulmonary ventilation and inspired concentration of agent.

1. Uptake of agent from the lung alveoli into the alveolar capillary blood depends on
2. Solubility of agent in blood, alveolar blood flow, and Alveolar-venous partial pressure difference.
3. For relatively the insoluble agents, $N_2O$—Nitrous oxygen and desflurane, slow uptake leads to fast rise in $F_A$.

Degree of solubility is expressed in the blood: gas solubility ratio, $lambda_{b/g}$:

The present invention makes usage of unobvious applications of several physics laws adapted to the pathophysiology of respiratory illnesses while combining two prior devices previously used separately, one being a hand held nebulizer and the other being a metered-dosage inhaler.

The present invention applies two pressurized canisters in one embodiment, and one canister in another embodiment. Both embodiments provide inhalable oxygen mixed with helium gas along with an anesthetic ability added to the gas mixture. Also, both embodiments provide a selected lower density gas mixture having oxygen gas within a canister. Different canisters may be had having differing concentrations of oxygen, not to exceed 35% in a preferred embodiment, but excluding higher oxygen concentrations when deemed sound and clinically necessary. Also, no greater helium concentration than 50% is adapted for use along with the present invention.

Said device as figures drawn display has means for allowing either of both canisters to be used for treating a person with respiratory insufficiency and or Chronic Obstructive Pulmonary Diseases, as seen in additional conditions as Emphysema, Asthma, Cystic Fibrosis, Croup and Bronchiolitis well as Cardiopulmonary complications either from a primary disease as seen in congestive heart failure or early stages of pulmonary edema. In addition, said device also has means by a uniquely designed for "attachment" to the present invention, this utilize additional anesthetic gas (es) held within a dissolvable envelope this for convince and ease as well as economy of space and cost. Said device is thus a greater rescue device for respiratory and some related cardiopulmonary diseases as cited in this application, especially for those with severe asthma and during bouts of crises in COPD.

Said additional present inventions 'attachment' is a cap that is held by means of a plastic or similar light weight strap having within its structure an opening with push fit to attach and or pull off to detach fitting onto the mouthpiece of the present inventions system. Within said attachment structure is a small encased battery for use with an encased heating element which is powered by said battery and a switch to activate said heating element. The present invention makes use of a switch that allows and directs the dispensed airway opener drug aerosol to follow one of two designed of paths, one directly from its canister to the user and or patient, the other to a medicine reservoir where the second canister jets gases from its canister via a valve that is depressed and so activated to release its contents of lowered gas density along with said airway opener medicine to the user/patient. This carries the aerosolized medicine from the medicine reservoir to the user/patient over a longer period of time. Also, the decreased density of the gas mixture allows further penetration and longer treatment times, thus providing greater affect in opening lower more distal airways blocked by secretions and/or inflammation. This is an improvement over previous metered-dosage inhalers (MDIs) which do not provided such extended treatment times, thus requiring a patient/user to use a hand held nebulized to effect such extended treatment times.

Said heating element is used to dissolve a wax and or sugar or similar non-toxic casing herein an envelope, said envelope containing a liquid and or similar dissolvable anesthetic gas encased is said envelope, that upon heating said envelope to above 100 degrees for less than a twenty to forty second period would dissolve said wax, and or sugar envelope containing said liquid anesthetic, allowing such anesthetic to be also heated and turn from liquid to vapor state to be inhaled by a user and or patient. Said attachment may or may not be used along with the unique selected oxygen, helium, and nitrogen gas mixture with adapted selected densities canister, depending upon the immediate needs of the user and or the patient.

Within said second pressurized canister as seen in one embodiment or as a single pressurized canister attached to the present invention as a specially adapted admixture of breathable enriched containing heliox and/or heliox nitrogen gases to assist and augment those individuals who have respiratory diseases as given such as—COPD, Asthma, Emphysema when during illness and or crises require such additional care prior to and in place of a hospital admittance. More especially when prior art rescue inhalers are unable to support such individuals or cannot provided nor add the additional benefits of the present invention. Such said gaseous admixture is specifically designed to use with the present invention being gases for inhalation for human and animals of a lower density than air breathed, being helium, oxygen and nitrogen placed under pressure within a refillable or discardable canister and in specific percentages designed for maintaining its gaseous admixture density, see examples provided in this application.

Said admixture of lowered density gaseous breathable gases is designed to ease both the work of breathing while simultaneously providing increased oxygen during a rescue treatment which prior art does not provide when portable, this as providing supplemental oxygen during rescue inhaler usage. In addition said gaseous admixtures are specifically used to increase the depth of airway penetration of aerosol medications inhaled and to increase the V/Q ratio to more normalize said mismatching by such benefits as greater penetration depth of said aerosol airway medication.

The mixture of gases having a density lower than that of air is comprised of gases having different concentrations or percentages within the mixture. In one embodiment, the mixture of gases is comprised of helium and oxygen gases (commonly known as "heliox") combined with $N_2$ gas. The mixture of gases is contained by a lightly pressurized canister that is attached to the rescue inhaler invention. In one embodiment, the heliox is not limited to having additional $N_2$ gas, where the helium and oxygen gases have lower concentrations than historically used.

In another embodiment, an anesthetic gas is used as a vaporized gas to be inhaled if selected in combination with oxygen gas. These combined gases allow for the pressurized aerosol drug to be delivered with optimal bronchodilator effects. Thus, the present invention can achieve both greater and safer airway opening for patients/users having diseases affecting such airway diameters and for patients/users who have increased work of breathing and who are entering a crisis stage of their illness, such as typically experienced by COPD patients during an infection or when under stress.

As stated above, there are two canisters, both under pressure, which are both attached to one device. One canister contains aerosolized drugs for combating respiratory diseases and insufficiency, such as albuterol sulfate.

The other canister contains a breathable gaseous admixture specifically designed for having a density lower than the density of air and being able to support oxygenation during a treatment, unlike previous devices. The breathable admixture is designed to increase the penetration depth of the aerosolized medicine from the other canister or form whatever container used, in order to alleviate several mechanisms that cause increased work of breathing, while supplementing and increasing the oxygen supply to improve the lower blood oxygen levels commonly seen in patients under respiratory difficulty. The breathable admixture is designed to provide more cardiorespiratory support during a respiratory crisis experienced by a user/patient.

$$Re = \frac{\rho V D}{\mu}$$

The velocity as seen in the Reynolds equation is a variable that cannot be accurately calculated simply by plugging in mathematical variables that arise per each breath this for the variables are both dynamic and alter breath per breath, it is conceptualized that the Reynolds number is adversely affected by having a too low gas density mixture inhaled. This at above 60% Helium to Oxygen mixture, for several clinical reasons, first no nitrogen adversely affects oxygen and gas wash out in such small airways and air sacs called "alveoli." Second, the region where laminar flow of inhaled air and or mixed gases is at the terminal and alveolar ducts, mass gas and or air flow is not realized to any relative beneficial extent, as such laminar flow is required and physiologically adapted, meaning to low of a gas density predisposes to accelerations in damaged lung parnychema as had in COPD populations. As such increasing V/Q inequalities rather than decreasing them. Additionally, any distal conducting airway having obstruction as where the flow is laminar, well may increase the resistances to exhaled flow impeding incoming fresh gases. Once again the higher the helium percentage as seen in prior clinical and or research trials also carry a greater viscosity of the helium/oxygen mixture compared with an air/oxygen mixture. Finally, the thermal conductivity of helium is high, which may well cause thermal-induced bronchial hyper-irritation in patients airways, also increasing less distal air sac exchanges leading further down a hypoxic pathway already well-traveled.

This is in effect opposite the large and main conducting airways where a large helium percentage in the gas mixture(s) would not only reduce the work of breathing but allow greater flows for less pressure, a much desired combination especially in the COPD populations. In easier terms, as the negative tug initiated by the person at inspiration, which has the highest level; the initial tug creating the highest gas flow rate at inspirations start, that said, the airways as they get smaller further down the conducting tree of the 23 generations has the highest velocity in the trachea and main bronchi's and down four to six more generations until entering the bronchioles at the 12 to 16 generation level there the velocity naturally drops off, as the gases move down the airways. However the reduction in diameter, by bronchoconstriction, infection, inflammation and loss of radial traction by damaged and destroyed lung tissue allows for early closure of conducting airways.

As such in smaller airways the flow increases the regional flow rate as such regains its increased flow rate then the initial inspiratory tug generates. This as the smaller conducting airways diameter is reduced by three to eight times from 29 mm down to 12 mm to 4 mm, and 0.5 mm as such gas(es) entering these smaller diameter conducting airways only enter the ones, the smaller bronchioles that are either open or the regional flow is laminar.

While the smaller conducting airways, for example the terminal bronchioles defined as the last part of the non-respiratory conductive airways entering the respiratory acinus, respiratory involved gas exchange in air sacs, typically having a diameter of 0.267 um and a length of 0.606 um, are filled with exudate and made even smaller in diameter by the inflammations of the infectious process clinically known in COPD gas and gases exchange become more dependent at the bronchioles on the laminar flow patterns of a more closely matched gas density to that of air do reach and follow a laminar flow to enter these semi-blocked bronchioles.

The present invention ensures a minor reduction in density from atmospheric air; meaning air typically adapted to by the individual living in that region allow by such slightly diminished gas(es) density of incoming gases to achieve a more laminar flow pattern then one with high concentrations of Helium where the inhaled gas mixture density is carefully selected to achieve such flow pattern and keep the velocity of the gases in such smaller diameter bronchioles less than that of a higher flow speed as had by to low a density gas mixture being breathed. This selected gas density to laminar flow pattern with reductions in V/Q mismatching is optimized, conceptualized by this Inventor being achieved and modified by both the PaO2, and PaCo2 measurements along with "arterial blood gas analysis" ("ABG,") this every other day. Said purpose for serial matching of the PaO2, and PaCo2 polargraphic data taken.

It is the clinical aim and goal by the present invention's usage of calculated lower gaseous mixtures density; such that the selected density of admixed gases being slightly less of atmospheric air inhaled, along with increased oxygen powering the present invention is to achieve such greater ventilatory gases to blood perfusion in COPD patients in crises; increasing V/Q matching designed to assist the as hereto clinically not dealt with breathing problems, this to increase removal of greater carbon dioxide gas and increased oxygenation in the COPD blood. As to high oxygen causes resorption atelectasis, i.e. collapse of air sac's unable to allow air entry, and to high helium allows approximately the exact same problem of collapse of the air sac by causing a slightly lower density then air the air sacs are filled better, with less pressure and prevent the resorption atelectasis with the coexisting COPD increases V/Q mismatching leading to greater ventilator failures amongst this population.

Gas mixtures having helium concentrations that are too high cause the gas mixture to have a density so low that the gas mixture's velocity is so high that the flow pattern is turbulent and less laminar which, while allowing for easing of the work of breathing in the critical gas exchange regions, also increases ventilatory to perfusion mismatching. The higher viscosity of the helium/oxygen mixture, compared with the air/oxygen mixture, could exert a contrary effect in areas of laminar flows. Indeed, in such areas, Poisseuille's law indicates that for a given flow, the pressure decrease is proportional to the viscosity. Additionally, the higher viscosity of the helium/oxygen mixture has to be considered during flow measurements." In simplified form, $\Delta P = r^4/v$.

Such turbulence occurs most especially in such destroyed lower lung regions, due to less available airways to carry the gas mixtures while simultaneously decreasing the airway diameter due to loss of supportive lung tissue maintaining radial traction on the conducting airways throughout the lung parenchyma while in the process of an infection and or asthmatic attack to the COPD patient. This is further supported by advanced research as documented by attempts to treat children with bronchiolitis using high Helium concentrations where in the upper regions of the conducting airways flow is highest and rapid laminar and slight turbulence of flow is seen, yet in the lower more distal conducting airways where the smallest conducting airways exist where turbulence causes ineffective ventilation and increases the anatomical; of course, increased dysfunctional shunts of the COPD populations adds more V/Q mismatching.

As such the flow needed at these levels prior to actual gas exchange is lamina flow which can be maintained by a higher density, more accurately a lower gas mixture density then air but closely to that of airs gas mixture as the present invention. Usages of to low a gas mixture inhaled in this patient population-during moderate to severe bouts in the COPD classifications, causes, becoming a turbulent flow of inhaled gas mixtures adjacent and entering the last nonconducting and conducting airways.

This decreases the ventilation and adds to the hypoxia and hypercapnia experienced by a patient and well lead the patient to require ventilator assistance, which is something to be avoided if possible due to the added damaging effects and lost time and cost factors placed upon the patient and hospital.

An additional aspect of the present invention is a cap that fits over the exiting mouthpiece section of the present invention, where within said cap are grooves that are set in a rotating collar such that said collar allows for the dispensing of contained meltable envelopes where within said meltable envelopes is an anesthesia liquid and or semi-solid form of anesthesia agent for both relaxation and increased bronchodilation. The cap is thus designed to combat inflammation and spasms within the tracheobronchial tree and other vessels within a patient/user.

$$\text{Poiseuille's Law: } n = \frac{\Delta P \pi r^4}{8lv}$$

Where:
P=pressure gradient between two ends of the tube in dynes/cm$^2$,
r=radius of the tube (in centimeters) raised to the fourth power,
l=length of the tube (in centimeters),
v=gas flow rate in cm$^3$/second, and
π/8 is a constant.
This equation can be simplified down to just a few of the variables to make the relations clear: $\Delta P = r^4/v$. This equation shows:

4. If the flow is halved, the resistance would be halved and the required pressure gradient would be greatly reduced.
5. If the flow rate remains constant, the pressure will vary inversely by the fourth power of the radius (in other words, for each unit of measure smaller the radius of the tube is, the pressure required to move the same amount of air through this smaller tube increases exponentially).
6. If the radius is reduced by half, resistance would be increased sixteen times.

The invention will next be described in connection with certain exemplary embodiments; however, it should be clear to those skilled in the art that various modifications, additions, and subtractions can be made without departing from the spirit or scope of the claims.

DETAILED DESCRIPTION OF THE INVENTION

Figure 1:
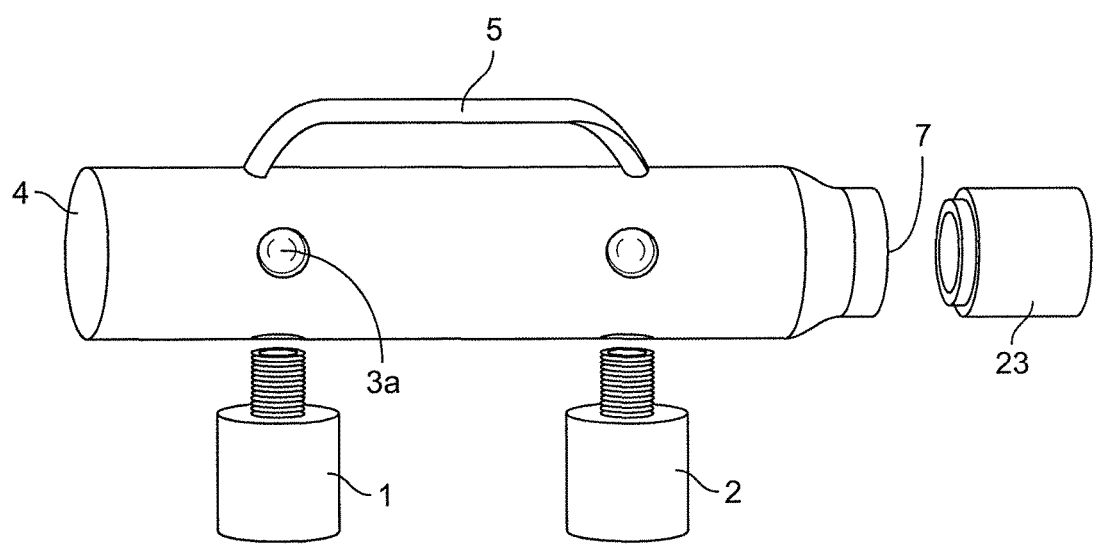
FIG. 1 shows a side view of an embodiment of the rescue inhaler of the present invention.
Figure 2:
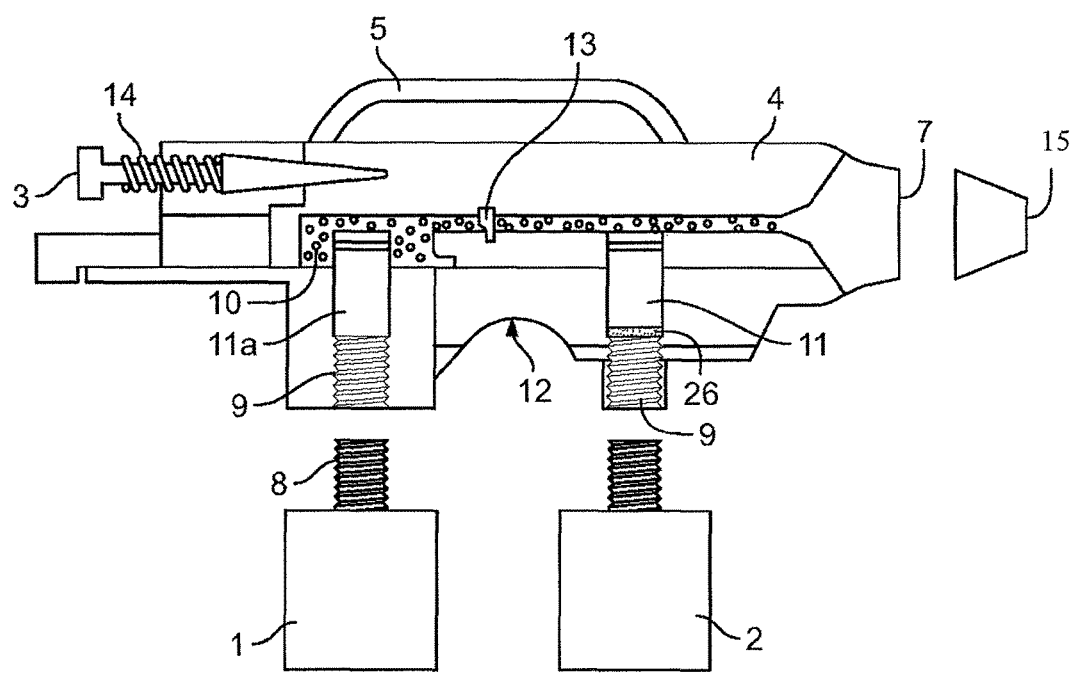
FIG. 2 shows a cut-through view of the internal components of an embodiment of the rescue inhaler of the present invention.

FIGS. 1 and 2 show an embodiment of the rescue inhaler with two attached canisters (1, 2). The first canister (1) is made of a metal material and the second canister (2) is made of a plastic or light metal material. The two canisters are screwed into the bottom of the rescue inhaler. The two canisters (1, 2) have threaded necks (8) for screwing them onto connector portals having corresponding threads (9).

The first canister (1) is a pressurized gas container having a mixture of at least three different gases including helium, oxygen, and nitrogen. The mixture of helium, oxygen, and nitrogen contained in the first canister (1) is designed for having a density that is slightly lower than the density of atmospheric air. By having a lower density than atmospheric air, the mixture of helium, oxygen, and nitrogen increases a patient's ease of breathing while simultaneously providing greater gas and aerosol deposition within the tracheobronchial tree of the patient and decreasing the ventilation to perfusion mismatching commonly experienced by COPD patients.

Different first canisters (1) containing different concentrations of helium, oxygen, and nitrogen can be interchangeably used with the rescue inhaler. As shown in FIG. 2, a first canister (1) having threads (8) can be screwed and unscrewed from the bottom of the rescue inhaler body (4) having threads (9). Thus, the rescue inhaler can be optimized to fit the particular needs of a particular patient/user by attaching a first canister (1) that has optimal concentrations of helium, oxygen, and nitrogen. Examples of gas mixtures that can be supplied by the first canister (1), each containing different concentrations of helium, oxygen, and nitrogen, are described below:

Example 1. % of He is 28% ($0.280 \times 0.178$)+% of $O_2$ is 23% ($0.230 \times 1.43$)+% of $N_2$ is 30% ($0.300 \times 1.25$)+19% air ($0.19 \times 1.29$ g/l)
$He=0.049+O_2=0.3289+N_2=0.375+Air=0.245=d$ avg.$=0.9979$ g/l Example 2. % of He is 30% ($0.300 \times 0.178$)+% of $O_2$ is 25% ($0.250 \times 1.43$)+% of $N_2$ is 30% ($0.300 \times 1.25$)+15% air ($0.15 \times 1.29$)=d avg.
$He=0.053+0.3575+0.375+0.193=d$ avg.$=0.9875$ g/l Example 3. % of He is 30% ($0.30 \times 0.178$)+% of $O_2$ is 40% ($0.40 \times 1.43$)+% of $N_2$ is 25% ($0.25 \times 1.25$)+5% air ($0.05 \times 1.29$)=d avg.
$He=0.0534+O_2=0.572+N_2=0.3125+Air=0.0645=d$ avg.$=1.108$ g/l Example 4. % of He is 20% ($0.02 \times 0.178$)+% of $O_2$ is 30% ($0.30 \times 1.43$)+% of $N_2$ is 40% ($0.40 \times 1.25$)+10% air ($0.10 \times 1.29$)=d avg.
$He=0.0356+O_2=0.429+N_2=0.5+air=0.129=d$ avg.$=1.0936$ g/l Example 5. % He is 35% ($0.350 \times 0.178$)+% $O_2$ is 35% ($0.350 \times 1.43$)+% of $N_2$ is 20% ($0.20 \times 1.25$)+10% air ($0.10 \times 1.29$)=d avg.
$He=0.062+O_2=0.501+N_2=0.25+air=0.129=d$ avg.$=0.942$ g/l Example 6. % He is 55% ($0.55 \times 0.178$)+% $O_2$ is 25% ($0.25 \times 1.43$)+% $N_2$ is 10% ($0.10 \times 1.25$)+10% air ($0.100 \times 1.29$)=d avg.
$He=0.098+O_2=0.357+N_2=0.125+air=0.129=d$ avg.$=0.709$ g/l In addition to these six examples, it is contemplated that additional mixtures of helium, oxygen and nitrogen having a lower density than atmospheric air are possible. Therefore, the rescue inhaler of the present invention is not limited to having canisters containing the six above examples of helium, oxygen and nitrogen concentrations.

The second canister (2) contains an aerosolized medicine that can be either an airway opening drug, called a bronchodilator, or an antibiotic medication. The second canister (2) may be comprised of a disposable plastic low weight container from which the aerosol medicine is pulled. Different aerosolized medicines may be utilized simply by switching the second canister (2) with another canister. For example, a second canister (2) having an unwanted aerosolized medicine can be unscrewed and a new second canister (2) having a desired aerosolized medicine can be screwed in its place.

Figure 3:
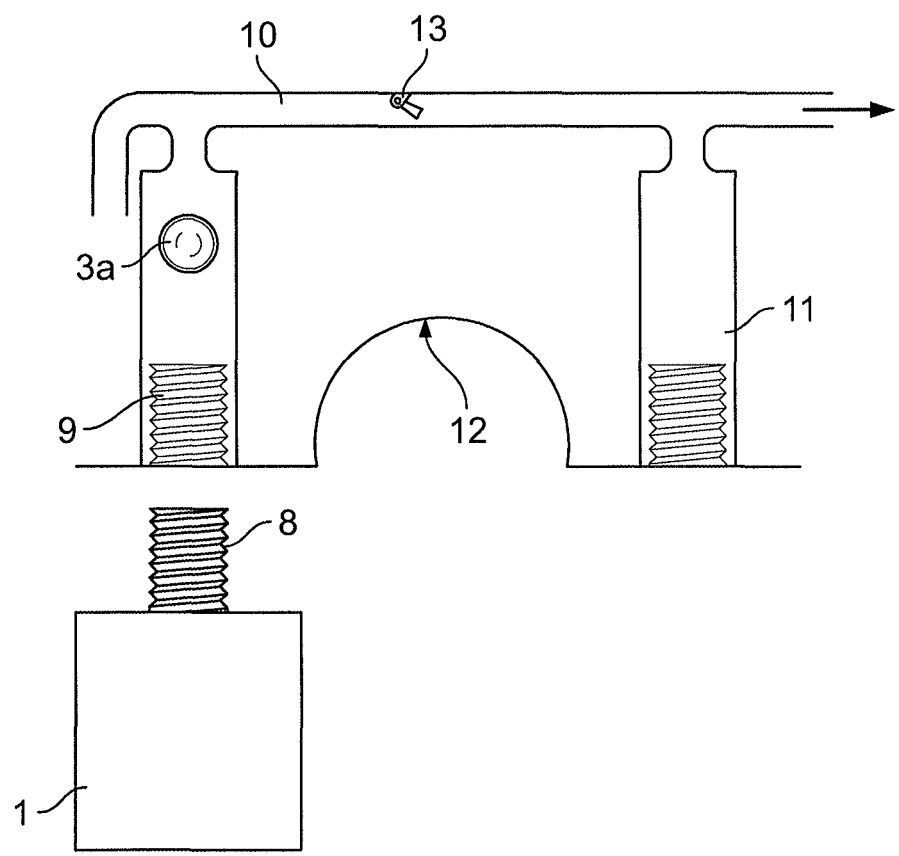
FIG. 3 shows a view of the gas and aerosol/medicine path in an embodiment of the rescue inhaler of the present invention.
Figure 5:
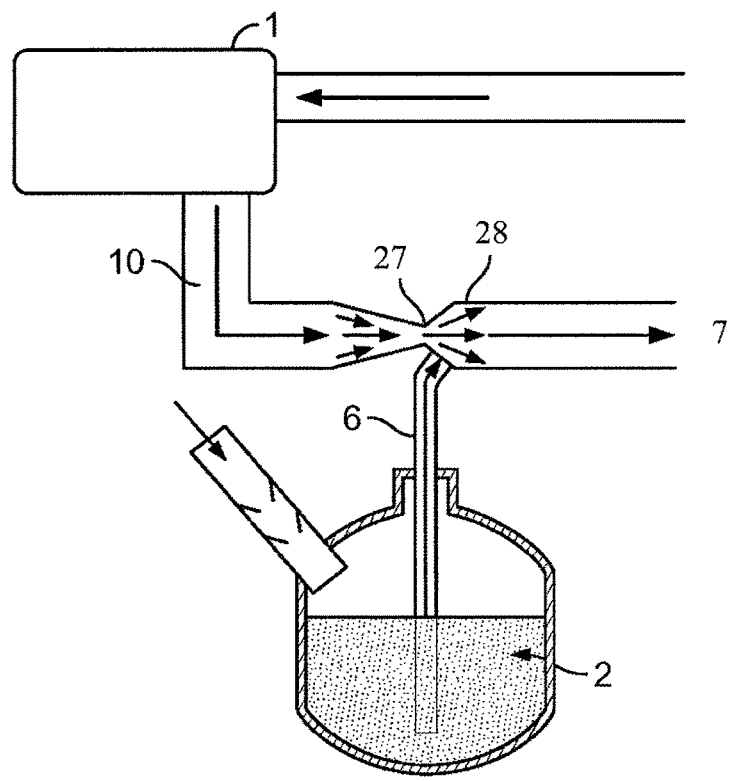
FIG. 5 shows a view of the gas and aerosol/medicine path in an embodiment of the rescue inhaler of the present invention.

FIG. 5 shows a capillary tube (6) for pulling the aerosol drug into gas path (10) (see FIGS. 2 and 3) which may contain a flow of the gas mixture released from the first canister (1). FIG. 3 shows an aerosol path (11) combining with the gas path (10) for discharging the mixture of gases released from the first canister (1) and the aerosol drug released from the second canister (2) into the mouth outlet (7) for inhalation by a patient/user of the rescue inhaler. FIG. 3 further shows a small flap valve (13) within the gas path (10) for preventing back flow when the rescue inhaler is not in use or during exhalation by the user into the rescue inhaler via the mouth outlet (7).

Figure 4A:
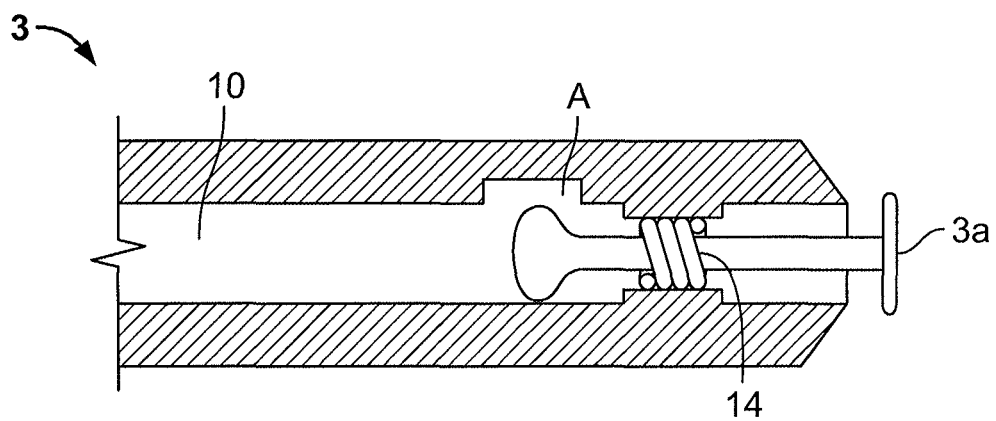
FIG. 4A shows a view of a Schrader type valve used in an embodiment of the rescue inhaler of the present invention in which the valve is unseated by a block of composite material.
Figure 4B:
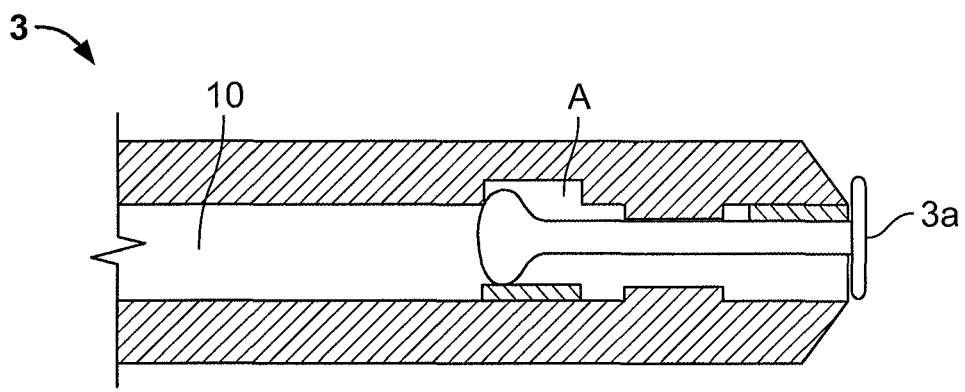
FIG. 4B shows a view of a Schrader type valve used in an embodiment of the rescue inhaler of the present invention in which the valve is seated.

FIG. 1 shows a manual push button (3a) for activating the Schrader type valve (3b), shown in FIG. 4, by unseating and seating the valve under spring pressure. This allows the contained gas mixture of the first canister (1) to be released. The gas mixture of the first canister (1) may be used to carry the aerosol drug released by the second canister (2) into the user's lungs. Alternatively, a user of the rescue inhaler may breathe only the gas mixture from the first canister (1) without having the aerosol drug released by the second canister (2). As another alternative, the user of the rescue inhaler may inhale only the aerosol drug released by the second canister (2) without having the gas mixture of the first canister (1) released.

As shown in FIG. 2, the mixture of gases is released into to the gas path (10) of the rescue inhaler. The mixture of helium, oxygen, and nitrogen are released from the first canister (1) by manual activation by pressing a push button (3a) such as the Schrader type valve (3b) shown in FIG. 4. By pressing the push button (3a), a valve compressing spring (14) is unseated. As shown in FIG. 5, this releases the gas mixture of helium, oxygen, and nitrogen into gas path (10) and this gas mixture is later combined with the aerosol drug exiting capillary tube (6) from the second canister (2). The gas mixture of helium, oxygen, and nitrogen combined with the aerosol drug is then discharged to the mouth outlet (7) of the rescue inhaler for inhalation by a patient/user.

FIGS. 1 and 2 show a grip handle (5) for a patient/user to slide their hand around for griping the rescue inhaler. FIG. 2 shows a cut through section (12) allowing a patient/user to grip the rescue inhaler in an even more secure manner. The cut through section (12) together with the handle (5) enables secure handling of the rescue inhaler.

FIG. 3 shows the first canister (1) which is a pressurized gas mixture of helium, oxygen, and nitrogen. As already described, it is contemplated that different canisters having different concentrations of helium, oxygen, and nitrogen can be interchangeably used with the rescue inhaler by screwing and unscrewing the different canisters onto the bottom of the rescue inhaler body (4). The gas mixture of helium, oxygen, and nitrogen released by the first canister (1) is designed to have a density that is slightly lower than the density of atmospheric air for improving a patient's ease of breath. However, care is taken to ensure that the density of helium, oxygen, and nitrogen is not too low so that velocity of the gas mixture entering the lungs of the patient is too fast causing an alveoli washout leading to further ventilation perfusion mismatching and consequently causing further respiratory distress.

FIG. 5 shows that by pressing the push button (3a), shown in FIG. 1, for activating the Schrader type valve (3b), shown in FIG. 4, the pressurized gas mixture from the first canister (1) flows though gas path (10), passes the hinged flap valve (13), shown in FIGS. 2 and 3, and then passes through a restricted orifice (27) to pull via suction liquid medicine up capillary tube (6) into a post restriction enlargement area (28) for discharging into mouth outlet (7) the combined gas mixture and medicine.

FIG. 3 shows the gas path (10) taken by the pressurized gases contained within the first canister (1) being a mixture of varying concentrations of helium, oxygen and nitrogen. The mixture of helium, oxygen, and nitrogen are designed to have particular concentrations to combat the pathophysiology of the patient/user and to have specific properties to maintain a near normal gas air density.

FIG. 4 shows an example of the Schrader type valve (3b) for use with the present invention. At position A, the valve seat is off the block of composite material allowing gas path (10) to freely move across the aerosol path (11) shown in FIG. 2.

In one embodiment of the invention, both the first and second canisters (1, 2) have a Schrader valve (3b) for controlling the release of their pressurized contents. In this embodiment, the Schrader valve (3b) for the second canister (2) is just above the aerosol path (11).

FIG. 5 provides a closer view of the gas path (10) which shows it flowing past a restricted orifice (27) and past a post restriction enlargement area (28) creating suction in capillary tube (6) and causing aerosol medicine to be suctioned up capillary tube (6). The aerosol medicine then flows along with the gas path (10) so that it is discharged out of the mouth outlet (7). This allows both the aerosol medicine and the mixture of helium, oxygen, and nitrogen to be inhaled by the patient/user.

The lower density and elevated oxygen concentration of the gas mixture from the first canister (1) combined with the aerosol medicine released by the second canister (2) allows greater aerosol medicine penetration depth into the lungs of users who suffer from COPD and also increases ventilation thereby improving oxygenation and carbon dioxide elimination in the user of the rescue inhaler. Moreover, this simultaneously decreases the work of breathing by the user and improves the dissemination of the gases and aerosol medicine deposition within the damaged COPD lung fields of the user.

By keeping the density of the gas mixture contained in the first canister (1) slightly below that of normal air, this slows down the velocity of the inhaled gases allowing for laminar flow in the most distal smallest communicating airways of the lungs of the user. This has the benefit of optimizing V/Q ratios over that of the prior art.

As seen by the present inventor, inhalation by emphysematous lungs of high concentrations of helium gas, above 60-65%, and high concentrations of oxygen, above 55%, creates alveolar gas washouts causing the closure of moderately and more distal lung fields and even slightly damaged air sacs (i.e., alveoli). Two factors are responsible for the worsening of V/Q ratios leading to greater and more frequent respiratory failures. The first factor is high helium gas concentrations which cause an increased gas flow velocity approaching, and in smaller airway regions, exceeding the Reynolds number which causes turbulence and ineffective ventilation. The second factor is air sac filler gases (e.g., nitrogen). For example, air comprises 20.94% oxygen which keeps the alveoli open, inflated, and intercommunicating alveoli "pores of khan" full by maintaining a proper density by virtue of both the gas density inhaled and the atmospheric pressure.

Referring to FIG. 4, no gas can flow past the valve (3b) when the valve (3b) is seated. The gas path (10) shown in FIG. 3 is still a path, but there is no flow of the gas mixture from the first container (1) until the spring (14) is manually compressed for unseating valve (3b). The second canister (2) may be manually compressed to activate the spray of the aerosol medicine as done in previously known metered-dosage inhalers. One compression of the second canister (2) produces one spay of typically 80 to 95 micrograms of aerosol medicine ejected into the aerosol path (11) and out into the common gas path for inhalation by the patient/user via the mouth outlet (7).

Alternatively, when the lower density gas mixture of helium, oxygen, and nitrogen from the first canister (1) flows through the gas path (10) and aspirates, the aerosol medicine is suctioned up capillary tube (6) slightly past restricted orifice (27) in an ongoing fashion until unneeded or the supply is exhausted. If either the supply of the pressurized gas mixture of the first canister (1) or the aerosolized medicine of the second canister (2) are exhausted, each canister can be replaced by another appropriate canister by unscrewing the exhausted canister and replacing it with a new canister which can be screwed onto the rescue inhaler body (4).

Figure 6:
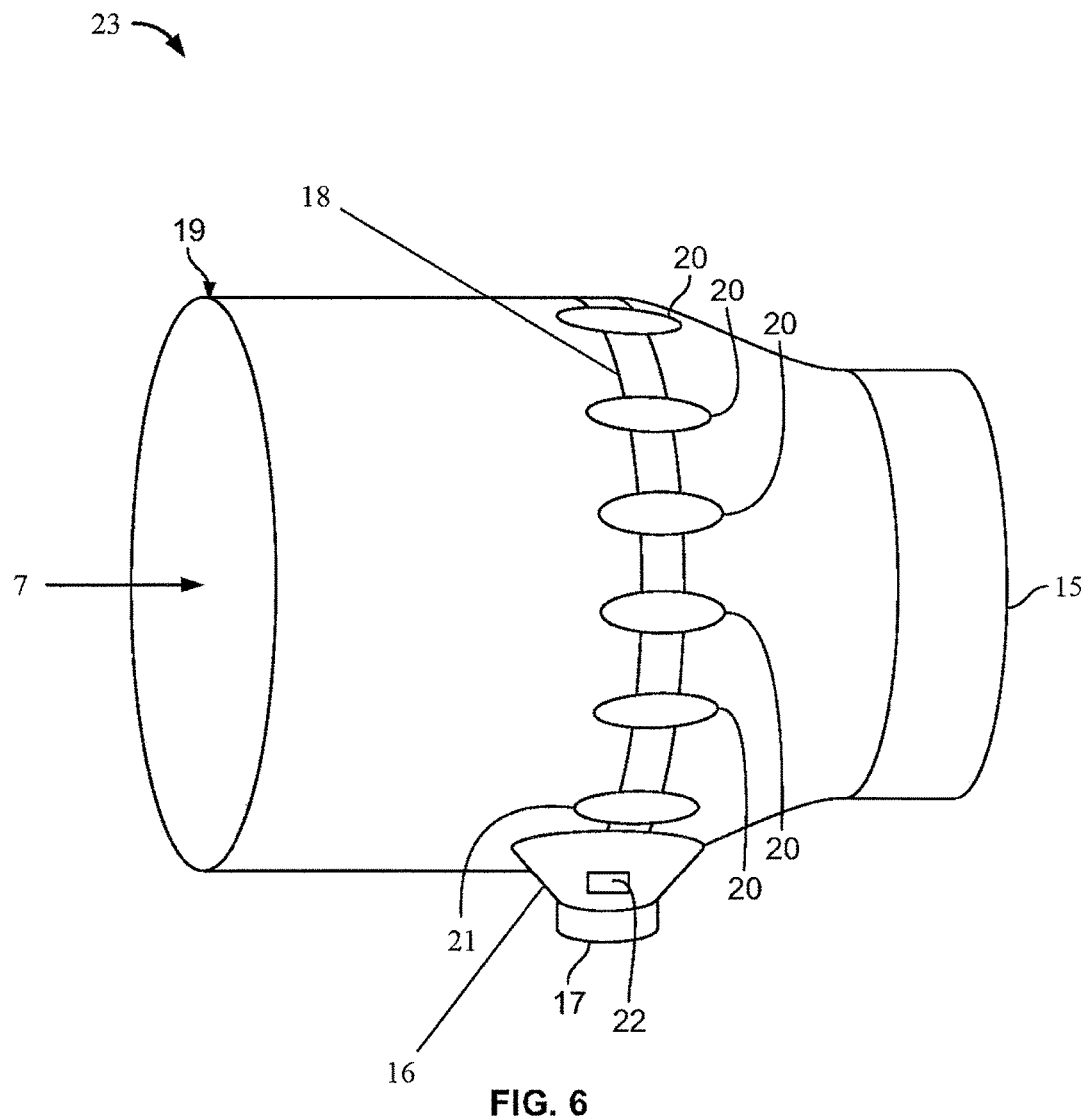
FIG. 6 shows an anesthetic attachment used in an embodiment of the rescue inhaler of the present invention.
Figure 7A:
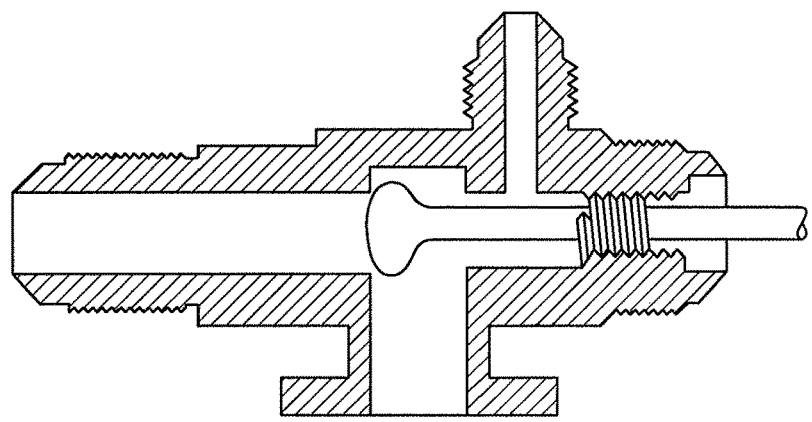
FIG. 7 shows a view of a Schrader type valve, (a) front seated, (b) back seated, and (c) mid-positioned, as used in an embodiment of the rescue inhaler of the present invention.
Figure 7B:
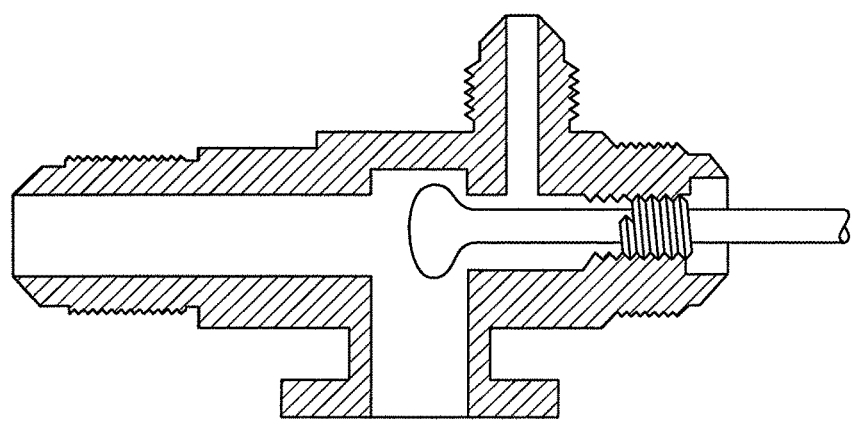
Figure 7C:
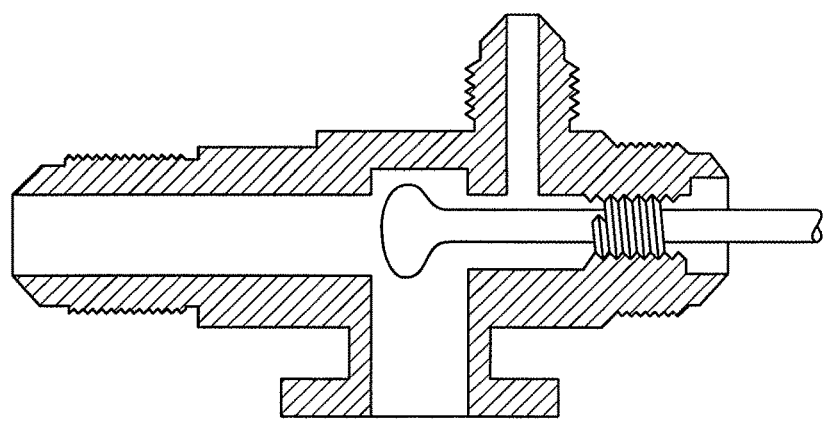

In an embodiment of the present invention, FIG. 6 shows an attachable anesthetic adapter (23) that can be connected to and disconnected from the rescue inhaler. The anesthetic adapter (23) fits over the mouthpiece of the rescue inhaler and is connected to the mouthpiece outlet (7) by a push-fit or is screwed into place. The anesthetic adapter (23) has its outer circumference (19) being a fixed outer surface slightly larger than the mouth outlet (7) so that it may be easily push-fitted or screwed onto the mouth outlet (7).

The anesthetic adapter (23) has an interior sliding ring (18) having attached pockets (20). A wax and or non-toxic sugar coated envelope (21) is dropped or placed into each pocket (20) on the sliding ring (18). Within each envelope (21) is an anesthetic in liquid/semi-solid state in a fixed amount. The liquid/semi-solid anesthetic may be readily vaporized by a heater (22) powered by a small insertable ion battery (17) for vaporizing an envelope (21) and freeing its contents for inhalation by the user at exit (15). The patient/user may inhale the vaporized anesthetic with or without any aerosol medicine from the second canister (2). Similarly, the patient/user may inhale the vaporized anesthetic with or without the low density gas mixture of helium, oxygen, and nitrogen from the first canister (1).

A pocket (20) on the sliding ring (18) matches up with an opening that has a small receptacle (16) below it allowing an envelope (21) held by pocket (20) to be dropped into the receptacle (16). The receptacle (16) is connected to a battery that heats up the sides and bottom of the receptacle (16) so that the envelope (21) containing the liquid and/or semi-solid anesthetic held by the receptacle (16) is also heated. The receptacle (16) is made of ceramic or other heat resistant material. The anesthetic contained in the wax and or non-toxic sugar coated envelope (21) is a fraction of the MAC that would cause laryngospasm and or loss of consciousness.

To receive treatment from the rescue inhaler, a patient/user having difficulty breathing either due to an asthmatic and/or emphysematous condition would take out the rescue inhaler, press the push button (3a) to release the Schrader type relief valve (3b), compress the second canister (2) containing aerosolized medicine, and inhale. The aerosolized medicine from the second canister (2) may be powered by the mixture of helium, oxygen, and nitrogen from the first canister (1) for providing increased medicine deposition farther into the diseased and problematic airways of the user, easing the user's work of breathing, and for providing supplemental oxygen. In view of these benefits, the rescue inhaler of the present invention allows for increased emergency rescue.

The second canister (2) is powered by gas driven either from the first canister (1) or by self-contained pressure whereby a user pushes the second canister (2) upwards to eject one spray, typically 80 to 90 micrograms of aerosolized medicine.

Figure 5A:
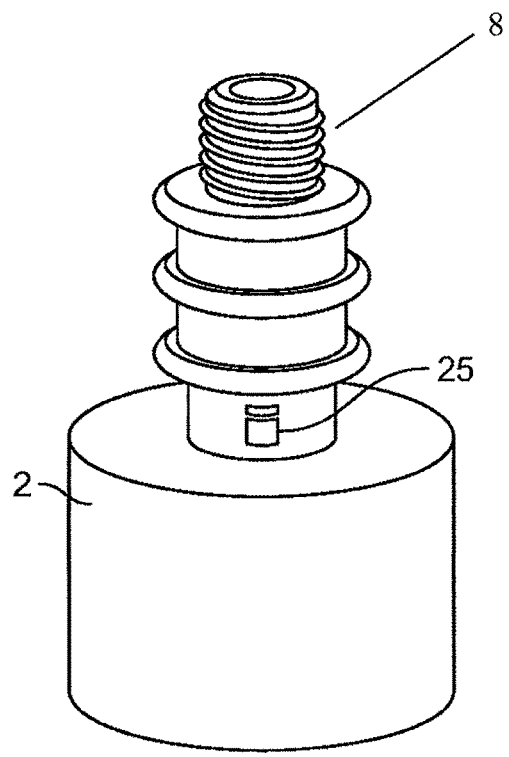
FIG. 5a shows a view of a secondary valve on the second canister in an embodiment of the rescue inhaler of the present invention.

Alternatively, if the second canister (2) is threaded past a red line (26) by screwing the external threads (8) of the second canister (2) past a threshold in the threads (9) of the rescue inhaler body (4), a cover of a secondary valve (25) shown in FIG. 5a is slid off keeping the secondary valve (25) opened into the gas path (10) generating suction via the restricted orifice (27) for sucking up the aerosolized medicine via capillary tube (6) and for continuously discharging the aerosolized medicine from the second canister (2) to the patient/user. Thus, if a patient has a severe asthma attack, the second canister (2) can be screwed past the red line (26), meaning all the way up the internal threads (9) of the rescue inhaler body (4), so that the aerosol medicine contained in the second canister (2) flows continuously up the aerosol path (11) and continuously flows into the gas path (10) for continuously discharging the aerosolized medicine to the patient/user.

Keeping the secondary valve (25) opened in the compressed condition allows for the ongoing spray of the aerosolized medicine from the second canister (2). The ongoing spray of aerosolized medicine is then powered to the mouth outlet (7) by the mixture of helium, oxygen, and nitrogen gas. The mixture of helium, oxygen, and nitrogen gas is emitted from the first canister (1) by pressing and holding the push button (3a) on the external body (4) of the rescue inhaler which compresses the valve spring (14) thereby activating the Schrader type valve (3b) by allowing the valve seat A to be unseated.

The push button (3a) acts as a safety mechanism by preventing inadvertent activation of the Schrader type valve (3b). The push button (3a) also provides a user with the ability to either continually keep the push button (3a) depressed, or to alternatively pause and press the push button (3a) over time for conserving the helium, oxygen, and nitrogen mixture. This also allows the user to judge the effects of the helium, oxygen, and nitrogen mixture combined with the aerosolized medicine over time, thus truly allowing patient/user full control over their treatment.

The second canister (2) must be screwed onto the threads (9) of the rescue inhaler body past a red line (26) that is marked on the outside of the body (4) of the rescue inhaler so that the red line (26) is visible to a user. This causes the sliding of a valve cover of a secondary opening (25) within the container neck of the second canister (2). This is shown in FIG. 5a. The cover of said valve when removed allows for contents of the second canister (2) to be sucked up into the gas path (10) of the rescue inhaler.

In view of the above, a user may use the present rescue inhaler invention intermittently, for example, to take a spray of the aerosolized medicine from the second canister (2) by depressing the second canister (2) one time as done with previously known metered-dosage inhalers. Alternatively, the user may use the first canister (1) for emitting a mixture of helium, oxygen, and nitrogen that is specifically designed to have a density that is slightly lower than the density of atmospheric air for breathing either alone or along with the aerosolized medicine sprayed from the second canister (2).

A user may use a continuous spray of the aerosolized medicine from the second canister (2) powered by the helium, oxygen, nitrogen gas mixture from the first canister (1) for a prolonged period (e.g., forty seconds or a minute and a half). The user may then stop the treatment to gage its effect over time. Such treatment not only eases the work of breathing for the user and supplies supplemental oxygen to the user, but also generates greater penetrating depth for the aerosolized medicine in the user's airways. The aerosolized medicine from the second canister (2) reaches farther down into the user's airways due to the mixture of gases (helium, oxygen, nitrogen) from the first canister (1) having a density that is slightly lower than the density of atmospheric air.

Additional embodiments and variations of the above described rescue inhaler invention are contemplated. For example, although the embodiments described above have two pressurized canisters (one containing a mixture of helium, oxygen, and nitrogen, the other containing aerosolized medicine), it is contemplated that there may be other embodiments having only one canister. In one particular embodiment, a rescue inhaler with only a single canister comprising a mixture of oxygen and helium gas along with an anesthetic ability added to the gas mixtures is contemplated.

Moreover, it is envisioned that different canisters having different concentrations of oxygen may be used with the present invention. Although, such concentrations of oxygen are not to exceed 35%, it is contemplated that higher oxygen percentages when deemed sound and clinically necessary may be used. It is further contemplated that different canisters with different concentrations of helium may be used with the present invention. Such concentrations of helium are generally not to exceed 50%.

An additional aspect of the present invention is an anesthetic adapter (23) acting as a cap that fits over or push fits onto the exiting mouthpiece section (7) of the present rescue inhaler invention. The anesthetic adapter (23) has pockets or grooves (20) that are set in a rotating collar or sliding ring

(18) such that the rotating collar or sliding ring (18) allows for the dispensing of meltable envelopes (21) contained within the pockets or grooves (20) when put into a position that is heated by a heating source (22) powered by a battery (17) as shown in FIG. 6. The meltable envelopes (21) have an anesthesia liquid and/or semi-solid form of anesthesia agent for both relaxation and increased bronchodilation. Moreover, the anesthesia agent in the meltable envelopes (21) also combats inflammation and spasms within the tracheobronchial tree and other vessels of the user.

In another embodiment, the rescue inhaler body (4) splits in half so that if a user desires to use the rescue inhaler as only a metered-dosage inhaler, the user can break the rescue inhaler body (4) into two halves and use only the half corresponding to the second canister (2) containing the aerosolized medicine. For example, if the user does not have a need for the first canister (1), the half pertaining to the first canister (1) having the helium, oxygen, and nitrogen gas mixture can be left at home so that the portable rescue inhaler is even more portable.

Additionally, the rescue inhaler could be sold in separate pieces so that a user, who only has a need for a metered-dosage inhaler, can buy the piece corresponding to the second canister (2) for administering an aerosolized medicine without having to buy the other piece corresponding to the first canister (1) for administering the helium, oxygen, and nitrogen gas mixture. Thus, the portable rescue can be made more economical for individual users based on their needs by selling pieces of the rescue inhaler body (4) separately. Moreover, if the user eventually develops a need for the first canister (1) containing a supply of the helium, oxygen, nitrogen gas mixture, the user can buy the piece corresponding to the first canister (1). Thus, the rescue inhaler is adaptable to a user's needs which may change over time.

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. Thus, the present invention should not be limited by any of the above-described exemplary embodiments, but should be defined only in accordance with the following claims and their equivalents.

In addition, it should be understood that the illustrated figures, which highlight the functionality and advantages of the present invention, are presented for example purposes only. The architecture of the present invention is sufficiently flexible and configurable, such that it may be utilized in ways other than that shown in the accompanying figures.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the present invention in any way.

The invention claimed is:

1. A rescue inhaler comprising:
a body having first and second connector portals;
a first canister attachable to the first connector portal storing a gas mixture comprising helium, oxygen, nitrogen, and air gases;
wherein the gas mixture has a density that is lower than the density of atmospheric air;
a second canister attachable to the second connector portal storing an aerosolized medicine;
wherein the aerosolized medicine stored in the second canister is sprayed into an aerosol path when the second canister attached to the second connector portal is threaded past a threshold; and
a push button located outside the body of the rescue inhaler for activating a valve for releasing the gas mixture of the first canister into a gas path;
wherein the gas mixture flowing in the gas path pulls the aerosolized medicine from the aerosol path into the gas path leading the aerosolized medicine and the gas mixture to be discharged out of a month outlet;
wherein the first and second canisters have threaded necks allowing the first and second canisters to be screwed onto corresponding threads of the first and second connector portals, respectively.

2. The rescue inhaler of claim 1, further comprising:
a flap valve within the gas path for preventing back flow when the rescue inhaler is not in use or during exhalation from a user into the rescue inhaler via the mouth outlet.

3. The rescue inhaler of claim 1, wherein different first canisters containing different concentrations of helium, oxygen, and nitrogen gas can be interchangeably attached to the first connector portal.

4. The rescue inhaler of claim 1, wherein different second canisters containing different aerosolized medicines can be interchangeably attached to the second connector portal.

5. The rescue inhaler of claim 1, wherein the aerosolized medicine stored in the second container is an airway opening drug, called a bronchodilator.

6. The rescue inhaler of claim 1, wherein the aerosolized medicine stored in the second container is an antibiotic medication.

7. The rescue inhaler of claim 1, wherein the valve for releasing the gas mixture of the first canister is a Schrader valve.

8. The rescue inhaler of claim 7, wherein the push button activates the Schrader valve by unseating the Schrader valve under spring pressure.

9. The rescue inhaler of claim 1, wherein the first canister is made of a metal material and the second canister is made of a plastic or metal material.

10. The rescue inhaler of claim 1, wherein the gas mixture released from the first canister carries the aerosol drug released from the second canister into a user's lungs.

11. The rescue inhaler of claim 1, wherein only the gas mixture from the first canister is released without having the aerosolized medicine released by the second canister.

12. The rescue inhaler of claim 1, wherein only the aerosolized medicine from second canister is released without having the gas mixture of the first canister released.

13. The rescue inhaler of claim 1, wherein
the gas mixture comprises helium having a concentration not greater than 55%, and oxygen having a concentration not greater than 40% for reducing the density of the gas mixture below the density of atmospheric air to achieve laminar flow in most distal communicating airways.

14. The rescue inhaler of claim 1, wherein the mixture of gas flowing in the gas path passes a restricted orifice creating suction in a capillary tube in the aerosol path,
sucking-up the aerosolized medicine in the capillary tube, leading the aerosolized medicine to flow with the gas mixture in the gas path, and leading the aerosolized medicine and the gas mixture to be discharged out of the mouth outlet.

15. The room inhaler of claim 1, wherein the rescue inhaler body is breakable into two halves, thereby physically separating a first half carrying the first canister from a second half carrying the second canister.

16. The rescue inhaler of claim 1, wherein the first and second connector portals are places on a first portion of the body, and wherein the body further comprises a grip handle on a second portion of the body, which is direct opposite to the first portion.

17. A rescue inhaler comprising:

a body having first and second connector portals;

a first canister attachable to the first connector portal storing a gas mixture comprising helium, oxygen, nitrogen, and air gases;

wherein the gas mixture has a density that is lower than the density of atmospheric air;

a second canister attachable to the second connector portal storing an aerosolized medicine;

wherein the aerosolized medicine stored in the second canister is sprayed into an aerosol path when the second canister attached to the second connector portal is pushed upwards;

a push button located outside the body of the rescue inhaler for activating a valve for releasing the gas mixture of first canister into a gas path;

wherein the gas mixture flowing in the gas path pulls the aerosolized medicine from the aerosol path into the gas path leading the aerosolized medicine and the gas mixture to be discharged out of a mouth outlet; and an attachable anesthetic adapter that fits over the mouth outlet;

wherein the anesthetic adapter comprises an interior sliding ring haying attached pockets;

wherein a wax or non-toxic sugar coated envelope is placed into each pocket on the sliding ring;

wherein each envelope has an anesthetic in liquid or semi-solid state form;

wherein a heater powered by a small insertable ion battery melts the envelope and vaporizes the anesthetic for inhalation.

18. The rescue inhaler of claim 17, wherein the vaporized anesthetic is inhaled with or without the aerosolized medicine from the second canister.

19. The rescue inhaler of claim 18, wherein the vaporized anesthetic is inhaled with or without the gas mixture from the first canister.

20. A rescue inhaler comprising;

a body having first and second connector portals;

a first canister attachable to the first connector portal storing a gas mixture comprising helium, oxygen, nitrogen, and air gases;

wherein the gas mixture has a density that is lower than the density of atmospheric air;

a second canister attachable to the second connector portal storing an aerosolized medicine; and wherein the aerosolized medicine stored in the second canister is sprayed into an aerosol path when the second canister attached to the second connector portal is threaded past a threshold;

a push button located outside the body of the rescue inhaler for activating a valve for releasing the gas mixture of the first canister into a gas path;

wherein the gas mixture flowing in the gas path pulls the aerosolized medicine from the aerosol path into the gas path leading the aerosolized medicine and the gas mixture to be discharged out of a mouth outlet;

wherein screwing the second canister past a line on the second connector portal opens a secondary valve on the second canister for continuously discharging the aerosolized medicine from the second canister.

* * * * *